(12) United States Patent
Mattern

(10) Patent No.: US 10,729,646 B2
(45) Date of Patent: Aug. 4, 2020

(54) NASAL PHARMACEUTICAL COMPOSITIONS FOR REDUCING THE RISKS OF EXPOSURE TO AIR POLLUTANTS

(71) Applicant: M et P Pharma AG, Emmetten (CH)

(72) Inventor: Claudia Mattern, Emmetten (CH)

(73) Assignee: M ET P PHARMA AG, Emmetten (CH)

( * ) Notice: Subject to any disclaimer, the term of this patent is extended or adjusted under 35 U.S.C. 154(b) by 0 days.

(21) Appl. No.: 16/016,335

(22) Filed: Jun. 22, 2018

(65) Prior Publication Data

US 2018/0296472 A1    Oct. 18, 2018

Related U.S. Application Data

(63) Continuation-in-part of application No. PCT/IB2018/050349, filed on Jan. 19, 2018.
(Continued)

(51) Int. Cl.
*A61K 9/00*  (2006.01)
*A61K 47/44*  (2017.01)
(Continued)

(52) U.S. Cl.
CPC .............. *A61K 9/0043* (2013.01); *A61K 9/06* (2013.01); *A61K 33/00* (2013.01); *A61K 45/06* (2013.01);
(Continued)

(58) Field of Classification Search
CPC ...... A61K 9/0043; A61K 39/06; A61K 47/26; A61K 45/06; A61K 33/00; A61K 47/44
See application file for complete search history.

(56) References Cited

U.S. PATENT DOCUMENTS 4,546,882 A    10/1985  Hsu et al.
5,002,597 A *   3/1991  Gielow ................. B01D 46/12
                                                    55/486
(Continued)

FOREIGN PATENT DOCUMENTS

WO    WO-97/44013 A1    11/1997
WO    WO-98/30245 A2     7/1998
(Continued)

OTHER PUBLICATIONS

Database WPI, Week 201028, Thomson Scientific (Apr. 2010) London GB, AN 2010-E08397, XP002779459.
(Continued)

*Primary Examiner* — Aradhana Sasan
*Assistant Examiner* — Quanglong N Truong
(74) *Attorney, Agent, or Firm* — Foley & Lardner LLP

(57) ABSTRACT

Described herein are methods for reducing the risks of exposure to air pollutants, comprising nasally administering to a subject in need thereof a composition that counteracts the effects of one or more air pollutants, wherein the composition is adapted for nasal administration. In some embodiments the composition comprises an agent that binds to one or more air pollutants, wherein the agent comprises one or both of nonporous silicon dioxide and porous silicon dioxide and/or the composition provides a physical barrier between one or more air pollutants and internal nasal surfaces. Also described are nasal compositions comprising an agent comprising one or both of nonporous silicon dioxide and porous silicon dioxide, a lipophilic or partly lipophilic vehicle, and a surfactant, wherein the composition is adapted for nasal administration. The compositions also may comprise other agents, such as an immunosuppressant. Also described are methods of making and using the compositions.

21 Claims, 2 Drawing Sheets

Related U.S. Application Data

(60) Provisional application No. 62/448,556, filed on Jan. 20, 2017, provisional application No. 62/517,369, filed on Jun. 9, 2017.

(51) Int. Cl.

| | | |
|---|---|---|
| *A61K 33/00* | (2006.01) | |
| *A61K 47/02* | (2006.01) | |
| *A61K 9/06* | (2006.01) | |
| *A61K 47/14* | (2017.01) | |
| *A61P 37/08* | (2006.01) | |
| *A61P 39/00* | (2006.01) | |
| *A61P 29/00* | (2006.01) | |
| *A61P 39/06* | (2006.01) | |
| *A61K 45/06* | (2006.01) | |
| *A61K 47/26* | (2006.01) | |

(52) U.S. Cl.
CPC .............. *A61K 47/02* (2013.01); *A61K 47/14* (2013.01); *A61K 47/26* (2013.01); *A61K 47/44* (2013.01); *A61P 29/00* (2018.01); *A61P 37/08* (2018.01); *A61P 39/00* (2018.01); *A61P 39/06* (2018.01)

(56) References Cited

U.S. PATENT DOCUMENTS

| | | | |
|---|---|---|---|
| 7,001,615 | B1 | 2/2006 | Singh et al. |
| 8,258,137 | B2 | 9/2012 | Augustijns et al. |
| 8,574,622 | B2 | 11/2013 | Mattern |
| 8,609,043 | B2 | 12/2013 | Mattern |
| 8,784,869 | B2 | 7/2014 | Mattern |
| 8,877,230 | B2 | 11/2014 | Mattern |
| 9,186,320 | B2 | 11/2015 | Mattern |
| 9,238,072 | B2 | 1/2016 | Mattern |
| 9,579,280 | B2 | 2/2017 | Mattern |
| 9,962,394 | B2 | 5/2018 | Mattern |
| 2006/0154069 | A1 | 7/2006 | Lin et al. |
| 2011/0244002 | A1 | 10/2011 | Shen et al. |
| 2012/0277202 | A1* | 11/2012 | Mattern ............... A61K 9/0043 514/178 |
| 2013/0040922 | A1 | 2/2013 | Kreppner et al. |
| 2015/0290217 | A1 | 10/2015 | Kreppner et al. |
| 2016/0089347 | A1 | 3/2016 | Kreppner et al. |
| 2018/0008615 | A1 | 1/2018 | Mattern |

FOREIGN PATENT DOCUMENTS

| | | | | |
|---|---|---|---|---|
| WO | WO-02/051379 | A2 | 7/2002 | |
| WO | WO-2007/041079 | A2 | 4/2007 | |
| WO | WO-2010/039560 | A2 | 4/2010 | |
| WO | WO-2012/156822 | A1 | 11/2012 | |
| WO | WO-2014/066856 | A1 | 5/2014 | |
| WO | WO-2015/066717 | A1 | 5/2015 | |
| WO | WO-2016/041992 | A1 | 3/2016 | |
| WO | WO-2017/023162 | A1 | 2/2017 | |
| WO | WO-2017042709 | A1 * | 3/2017 | .......... B01J 20/3217 |
| WO | WO-2017/208209 | A1 | 12/2017 | |

OTHER PUBLICATIONS

International Search Report dated Apr. 9, 2018 in application No. PCT/IB2018/050349.

International Search Report dated Jul. 26, 2017 in application No. PCT/IB2017/053288.

Lai, et al., "A Mesoporous Silica Nanosphere-Based Carrier System with Chemically Removable CdS Nanoparticle Caps for Stimuli-Responsive Controlled Release of Neurotransmitters and Drug Molecules," j. Am. Soc. Chem., vol. 125, No. 15, pp. 4451-4459 (Mar. 2003).

Martinez-Carmona, et al., "Smart Mesoporous Nanomaterials for Antitumor Therapy, Nanomaterials," vol. 5, pp. 1906-1937 (Nov. 2015).

Office Action dated Apr. 20, 2018 in U.S. Appl. No. 15/612,454 (US 2018-0008615).

Sun, "Mesoporous silica nanoparticles for applications in drug delivery and catalysis," a dissertation submitted to the graduate faculty in partial fulfillment of the requirements for the degree of Doctor of Philosophy, 118 pages (2012).

Vallet-Regi, et al., "Biomedical Applications of Mesoporous Ceramics: Drug Delivery, Smart Materials and Bone Tissue Engineering," 16 pages (2013).

Office Action dated Apr. 3, 2020, in U.S. Appl. No. 15/612,454.

* cited by examiner

NASAL PHARMACEUTICAL COMPOSITIONS FOR REDUCING THE RISKS OF EXPOSURE TO AIR POLLUTANTS

CROSS-REFERENCE TO RELATED PATENT APPLICATIONS

This application is a continuation-in-part of PCT/IB2018/050349, filed Jan. 19, 2018, which claims priority under 35 USC § 119(e) to U.S. Provisional Application 62/448,556, filed Jan. 20, 2017, and U.S. Provisional Application 62/517,369, filed Jun. 9, 2017, the entire contents of which are incorporated herein by reference.

TECHNICAL FIELD

Described herein are nasal pharmaceutical compositions that counteract the effects of one or more air pollutants, wherein the composition is adapted for nasal administration. Also described herein are methods of making and using nasal pharmaceutical compositions for reducing the risks of exposure to air pollutants.

BACKGROUND

Air pollution is considered to be a global health crisis that kills more people than malaria and HIV/Aids combined. It has been linked to a variety of health conditions, including respiratory conditions, cardiovascular conditions, neurodegenerative conditions, and developmental conditions. It is also one of the top environmental risk factors for premature death. Indeed, the International Energy Agency estimated in June 2016 that 6.5 million deaths per year are linked to air pollution, with the number set to increase significantly in the coming decades. Thus, there is a need for compounds and methods for reducing the risks of exposure to air pollutants.

SUMMARY OF THE INVENTION

Described herein are methods for reducing the risks of exposure to air pollutants, comprising nasally administering to a subject in need thereof a composition that counteracts the effects of one or more air pollutants, such as composition comprising an agent that binds to one or more air pollutants and/or a composition that provides a physical barrier between one or more air pollutants and internal nasal surfaces. In some embodiments, the agent comprises silicon dioxide, such as one or more of nonporous silicon dioxide and porous silicon dioxide.

In some embodiments, the air pollutants comprise one or more of gaseous components and particulate components. In some embodiments, the air pollutants comprise gaseous components comprising one or more of sulfur dioxide, carbon monoxide, nitrogen oxides, ozone, ammonia (NH3), volatile organic compounds (VOC), and chlorofluorocarbons (CFCs). In some embodiments, the air pollutants comprise particulate components comprising one or more of solid particles and liquid particles. In some embodiments, the air pollutants comprise particulate components comprising one or more of fly ash, volcanic ash, soil particles, sea salt, dust, dessicated cellular debris, spores, pollen, bacteria, combustion products, hydrocarbons, and toxic metals. In some embodiments, the air pollutants comprise one or more of nitrogen oxides, carbon monoxide, sulphur oxides, sulfates, nitrates, ammonium, chloride, trace metals, carbon, ozone, chlorinated hydrocarbons, brominated hydrocarbons, polynuclear hydrocarbons, benzopyrene, aldehydes, peroxylacyl nitrates, butanedione soot, 1,3-butanediene, arsenic, and selenium.

In any embodiments, the risks of exposure to air pollutants may comprise health problems associated with one or more of the cardiovascular system, the respiratory system, the nervous system, and the reproductive system.

In any embodiments, the agent may comprise colloidal silicon dioxide. In some embodiments, the agent comprises one or more of microporous silicon dioxide, mesoporous silicon dioxide, and macroporous silicon dioxide.

In some embodiments, the composition further comprises one or more of (i) a lipophilic or partly lipophilic vehicle and (ii) a surfactant. In some embodiments, the composition comprises a lipophilic or partly lipophilic vehicle comprising an oil or a mixture of oils, fatty acid esters, medium chain triglycerides, glycerol esters of fatty acids, polyethylene glycol, phospholipids, white soft paraffin, or combinations of two or more thereof. In some embodiments, the composition comprises an oil or mixture of oils comprising vegetable oil, castor oil, hydrogenated castor oil, soybean oil, sesame oil, peanut oil, or combinations of two or more thereof. In some embodiments, the composition comprises oil or mixture of oils comprising castor oil. In some embodiments, the composition comprises fatty acid esters comprising ethyl oleate, oleyl oleate, isoproyl myristate, or combinations of two or more thereof. In some embodiments, the composition comprises a surfactant comprising apricot kernel oil PEG-6-esters, lecithin, fatty acid esters of polyvalent alcohols, fatty acid esters of sorbitanes, fatty acid esters of polyoxyethylenesorbitans, fatty acid esters of polyoxyethylene, fatty acid esters of sucrose, fatty acid esters of polyglycerol, oleoyl polyoxylglycerides, oleoyl macrogolglycerides, sorbitol, glycerine, polyethylene glycol, macrogol glycerol fatty acid ester, or combinations of any two or more thereof. In some embodiments, the composition comprises a surfactant comprising apricot kernel oil PEG-6-ester. In some embodiments, the composition comprises one or more of castor oil and apricot kernel oil PEG-6-esters. In some embodiments, the composition consists essentially of colloidal silicon dioxide, castor oil, and apricot kernel oil PEG-6-esters.

Also described herein are nasal compositions comprising a porous agent that binds to one or more air pollutants, a lipophilic or partly lipophilic vehicle, and a surfactant, wherein the composition is adapted for nasal administration. In some embodiments, the composition is in the form of a gel. In some embodiments, the porous agent is dispersed in an oil mixture. In some embodiments, the composition provides a physical barrier between one or more air pollutants and internal nasal surfaces In any embodiments, the composition comprises (e.g., the porous agent is selected from) one or more agents comprising a material selected from inorganic porous materials, organic-inorganic hybrids, organic polymers, and complexing agents. In some embodiments, the composition comprises (e.g., the porous agent is selected from) an agent comprising an inorganic porous material selected from microporous silicon dioxide, mesoporous silicon dioxide, macroporous silicon dioxide, polyorganosiloxanes, pharmaceutical clays, silicon dioxide nanotubes, silicon dioxide gel, magnesium alumosilicate, anhydrous calcium phosphate, and calcium carbonate. In some embodiments, the composition comprises an agent comprising colloidal silicon dioxide. In some embodiments, the composition comprises an agent comprising an organic-inorganic hybrid that is a metal-organic framework. In some embodiments, the composition comprises (e.g., the porous agent is selected from) an agent comprising an organic polymer formed by a carbon-carbon coupling reaction, wherein the organic-inorganic hybrid comprises non-metallic elements. In some embodiments, the composition comprises (e.g., the porous agent is selected from) an agent comprising a complexing agent that is an adsorbent selected from β-cyclodextrin-based porous silicon dioxide, α-cyclodextrin-based porous silicon dioxide, hydroxpropyl-β-cyclodextrin-based porous silicon dioxide, and porous materials based on other adsorbents.

In some embodiments, the agent is functionalized with thiol groups, amine groups, crown ethers, quaternary alkyl amines, alkyl chains, alkoxysilanes, fluorenylmethoxycarbonyl-modified organosilanes, hydrophobic groups, mercaptopropyl groups, aminopropyl groups, hydroxypropyl groups, phenyl groups, or combinations of two or more thereof.

In any embodiments, the porous agent may comprise pores that have a longest diameter in any dimension of less than 2 nm, from 2 nm to 50 nm, or larger than 50 nm.

Also described herein are nasal compositions comprising an agent that binds to one or more air pollutants, a lipophilic or partly lipophilic vehicle, and a surfactant, wherein the composition is adapted for nasal administration, and wherein the agent comprises nonporous silicon dioxide. In some embodiments, the nonporous silicon dioxide is colloidal silicon dioxide. In some embodiments, the composition provides a physical barrier between one or more air pollutants and internal nasal surfaces Also described herein are nasal compositions comprising (a) from about 0.5% to about 50% w/w of a mesoporous silicon dioxide agent, based on the weight of the composition, (b) from about 50% to about 98% w/w of castor oil, based on the weight of the composition, and (c) from about 0.5% to about 20% w/w apricot kernel oil PEG-6-esters, based on the weight of the composition. In some embodiments, the composition consists essentially of the mesoporous silicon dioxide agent, the castor oil, and the apricot kernel oil PEG-6-esters. In some embodiments, the composition provides a physical barrier between one or more air pollutants and internal nasal surfaces Also provided are nasal compositions comprising an agent comprising nonporous silicon dioxide or porous silicon dioxide, a lipophilic or partly lipophilic vehicle, and a surfactant, wherein the composition is adapted for nasal administration, and wherein the agents binds to one or more air pollutants and/or provides a physical barrier between one or more air pollutants and internal nasal surfaces. In some embodiments, the agent binds to one or more air pollutants. In some embodiments, the agent provides a physical barrier between one or more air pollutants and internal nasal surfaces. In some embodiments, the agent binds to one or more air pollutants and provides a physical barrier between one or more air pollutants and internal nasal surfaces.

Also provided are nasal compositions comprising an immunosuppressive agent. In some embodiments, the immunosuppressive agent comprises one or more selected from antibodies against a cytokine selected from IL-2, IL-4, IL-5, IL-13, and TNFα, anti-IgE antibodies, glucocorticoids, antibiotics, polysaccharides, and antihistamines.

Also provided are methods of making a composition as described herein comprising mixing an agent as described herein, a lipophilic or partly lipophilic vehicle, and a surfactant. In some embodiments, the method comprises (a) preparing a mixture comprising the lipophilic or partly lipophilic vehicle and the surfactant, and then (b) adding the agent to the mixture.

Also provided are methods of reducing inflammation or reducing the risk of inflammation in a subject in need thereof, comprising nasally administering to a subject in need thereof a composition comprising an agent that binds to one or more air pollutants, wherein the agent comprises one or more of nonporous silicon dioxide and porous silicon dioxide, and/or a composition that provides a physical barrier between one or more air pollutants and internal nasal surfaces.

Also provided are methods of reducing inflammation or reducing the risk of inflammation in a subject in need thereof, comprising nasally administering to a subject in need thereof a composition comprising one or more of nonporous silicon dioxide and porous silicon dioxide.

Also provided are methods of reducing serum IgE levels in a subject, comprising nasally administering to a subject in need thereof a composition comprising one or more of nonporous silicon dioxide and porous silicon dioxide.

Also provided are methods of reducing serum TNF-α levels in a subject, comprising nasally administering to a subject in need thereof a composition comprising one or more of nonporous silicon dioxide and porous silicon dioxide.

Also provided are methods of reducing serum MIP-2 levels in a subject, comprising nasally administering to a subject in need thereof a composition comprising one or more of nonporous silicon dioxide and porous silicon dioxide.

Also provided are compositions as described herein for use in reducing the risks of exposure to air pollutants, reducing inflammation or reducing the risk of inflammation, reducing serum IgE levels in a subject, reducing serum TNF-α levels in a subject, reducing serum MIP-2 levels in a subject.

Also provided are uses of an agent as described herein in the manufacture of a medicament for reducing the risks of exposure to air pollutants, reducing inflammation or reducing the risk of inflammation, reducing serum IgE levels in a subject, reducing serum TNF-α levels in a subject, reducing serum MIP-2 levels in a subject.

BRIEF DESCRIPTION OF THE DRAWINGS

FIG. 2A shows a positive impact on body weight. FIG. 2B shows protection against an increase in serum IgE levels induced by exposure to dust. FIG. 2C shows protection against an increase in BAL LDH levels induced by exposure to dust. FIG. 2D shows protection against an increase in BAL TNF-α levels induced by exposure to dust. FIG. 2E shows a trend towards protection against an increase in BAL MIP2 levels induced by exposure to dust.

DETAILED DESCRIPTION

Definitions

Figure 1:
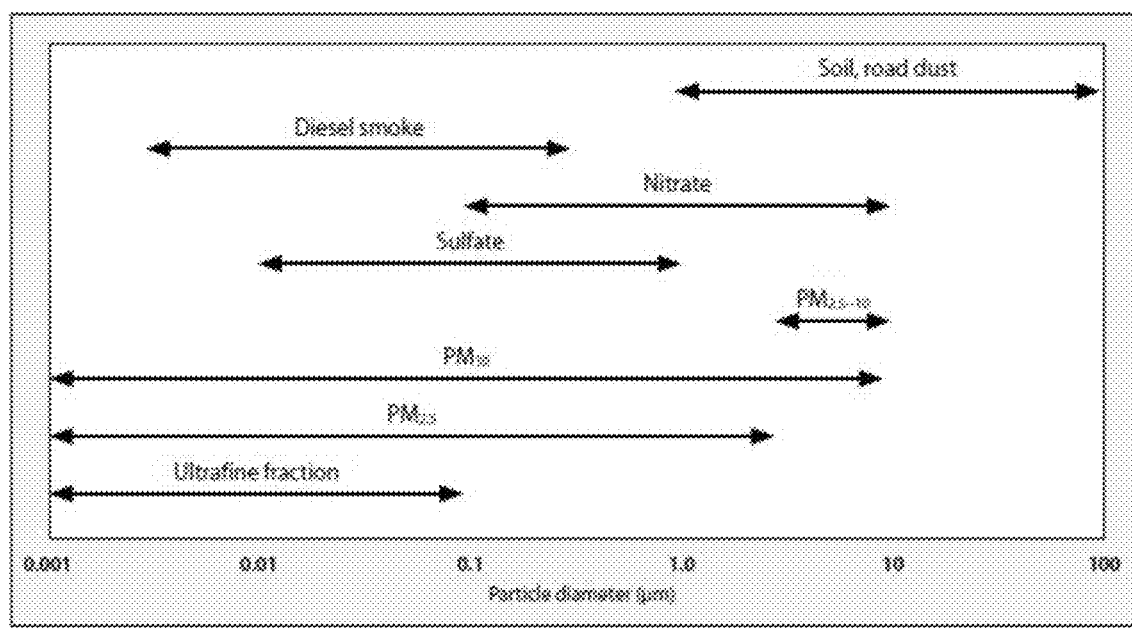
FIG. 1 depicts particle sizes of some constituents and forms of air pollution.

Technical and scientific terms used herein have the meanings commonly understood by one of ordinary skill in the art to which the present invention pertains, unless otherwise defined. Reference is made herein to various methodologies known to those of ordinary skill in the art. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted. Publications and other materials setting forth such known methodologies to which reference is made are incorporated herein by reference in their entireties as though set forth in full.

As used herein, the singular forms "a," "an," and "the" designate both the singular and the plural, unless expressly stated to designate the singular only.

The term "about" means that the number comprehended is not limited to the exact number set forth herein, and is intended to refer to numbers substantially around the recited number while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the term "consisting essentially of" as it relates to compositions as described herein means that specific agents, vehicles, surfactants, and viscosity-regulating agents are not present in the composition unless their presence is specifically mentioned.

As used herein, "subject" denotes any mammal, including humans. A subject may be exposed to, or at risk of exposure to, air pollutants, may be suffering from or at risk of developing a condition that can be treated or prevented with a composition that binds one or more air pollutants, or may be reducing the risks of exposure to air pollutants for health maintenance purposes.

As used herein, the phrase "effective amount" means an amount of composition that provides the specific effect for which the composition is administered. It is emphasized that an effective amount of the composition will not always be effective in ameliorating the risks of air pollutants described herein, even though such amount is deemed to be an effective amount by those of skill in the art. For convenience only, exemplary effective amounts are provided below with reference to adult human subjects. Those skilled in the art can adjust such amounts in accordance with standard practices as needed to treat a specific subject and/or condition/disease.

As used herein, "internal nasal surfaces" refers to surfaces of the nasal cavity, such as mucosal surfaces of the nasal cavity.

Nasal Compositions

Provided herein are nasal compositions comprising an agent that binds to one or more air pollutants and/or nasal compositions that provide a physical barrier between one or more air pollutants and internal nasal surfaces (e.g., that "blocks" one or more air pollutants). Also provided are methods of making and using such nasal compositions.

One entry point in the body for air pollutants is the nasal cavity. Air pollutants can, e.g., be inhaled, can accumulate on mucus in the nasal cavity, and/or can be absorbed in the nasal mucosa. Air pollutants that enter the body via the nasal cavity can then enter the upper respiratory tract or lungs, systemic circulation, and/or the brain (e.g., by crossing the blood brain barrier or via the olfactory and/or trigeminal nerve pathways).

By "nasal compositions" is meant compositions suitable for, or adapted for, nasal delivery, including intra-nasal delivery. The specific form of the nasal composition is not limited. In some embodiments, the nasal composition is in the form of a solution, suspension, dispersion, emulsion, or gel. In some embodiments, the composition is in the form of an oily liquid. In some embodiments, the composition is non-aqueous or water-free. (As used herein, "water-free" means that the composition is formulated without water, although trace amounts may be present.) In some embodiments, the composition comprises a water-free, semi-solid phase. In some embodiments, the composition is a hydrophilic gel or an emulgel (i.e., an emulsion incorporated in a gel base). In some embodiments, the composition is a hydrophobic gel, such as an oleogel or an organogel. In some embodiments, the composition comprises a three-dimensional, viscoelastic gel with small molecular weight organogelators (e.g., <900 Da) and/or polymeric gelators. In some embodiments, the composition is spreadable.

The nasal compositions described herein comprise an agent that binds to one or more air pollutants and/or that provides a physical barrier between one or more air pollutants and internal nasal surfaces. In some embodiments, the compositions further comprise a vehicle. Additionally or alternatively, in some embodiments, the compositions further comprise a viscosity-regulating agent. Additionally or alternatively, in some embodiments, the compositions further comprise a surfactant. Additionally or alternatively, in some embodiments, the compositions comprise an agent embedded in a gel network, such as a hydrophobic gel.

The nasal composition or a component thereof may bind to one or more air pollutants. The nasal composition or a component thereof may provide a physical barrier between one or more air pollutants and internal nasal surfaces. The nasal composition or a component thereof may bind to one or more air pollutants and provide a physical barrier between one or more air pollutants and internal nasal surfaces.

Agents that Bind Air Pollutants

As noted above, the nasal compositions described herein comprise an agent that binds to air pollutants and/or provides a physical barrier between one or more air pollutants and internal nasal surfaces. The agent may be a nonporous or porous material that can bind to air pollutants. In some embodiments, the agent comprises a nonporous material. In some embodiments, the agent comprises a porous material. In some embodiments, the composition comprises both a nonporous agent and a porous agent. In some embodiments, the air pollutant can bind onto surfaces of the agent, including surfaces located inside pores of the agent when a porous agent is used. In some embodiments with a porous agent, the porous agent acts as a matrix for the air pollutant.

In some embodiments, the agent comprises particles (e.g., nonporous or porous particles). Without being bound by theory, it is believed that even small and large particles can be effective by fixing them in a gel network using chemical and/or physical bonds, such as hydrogen-bonding and van der Walls forces. In any embodiments where the agent comprises particles, the particles may have a longest diameter in any dimension of from about 0.5 µm to about 350 µm, such as from about 50 µm to about 300 µm, about 100 µm to about 250 µm, about 150 µm to about 200 µm, or about 3 µm to about 35 µm. In some embodiments, the longest diameter is from 0.5 µm to 350 µm, such as from 50 µm to 300 µm, 100 µm to 250 µm, 150 µm to 200 µm, or 3 µm to 35 µm. In some embodiments, the particles have a longest diameter of about 0.5 µm, about 0.8 µm, about 1 µm, about 2 µm, about 3 µm, about 5 µm, about 10 µm, about 35 µm, about 60 µm, or about 150 µm. In some embodiments, the particles have a longest diameter of 0.5 µm, 0.8 µm, 1 µm, 2 µm, 3 µm, 5 µm, 10 µm, 35 µm, 60 µm, or 150 µm.

In some embodiments, the particles have a mean diameter of from about 0.5 µm to about 350 µm, such as from about 50 µm to about 300 µm, about 100 µm to about 250 µm, about 150 µm to about 200 µm, or about 3 µm to about 35 µm. In some embodiments, the mean diameter is from 0.5 µm to 350 µm, such as from 50 µm to 300 µm, 100 µm to 250 µm, 150 µm to 200 µm, or 3 µm to 35 µm. In some embodiments, the median diameter of the particles in a composition is about 0.5 µm, about 0.8 µm, about 1 µm, about 2 µm, about 3 µm, about 5 µm, about 10 µm, about 35 µm, about 60 µm, or about 150 µm. In some embodiments, the median diameter of the particles in a composition is 0.5 µm, 0.8 µm, 1 µm, 2 µm, 3 µm, 5 µm, 10 µm, 35 µm, 60 µm, or 150 µm.

A composition as described herein may comprise any suitable amount of agent that binds air pollutants and/or provides a physical barrier between one or more air pollutants and internal nasal surfaces, such as any amount effective to reduce the risks of exposure to air pollutants while still being suitable for nasal administration. In some embodiments, the composition comprises from about 0.5% to about 30% w/w, about 1% to about 20% w/w, about 5% to about 15% w/w, or about 8% to about 10% w/w agent, based on the total weight of the composition. In some embodiments, the composition comprises from 0.5% to 30% w/w, 1% to 20% w/w, 5% to 15% w/w, or 8% to 10% w/w agent, based on the total weight of the composition.

In some embodiments, the agent may be selected and/or prepared to bind to specific air pollutants or types of air pollutants. In some embodiments, the agent may be selected and/or prepared to bind particles originating from manmade sources. In some embodiments, the agent may be selected and/or prepared to bind particles originating from natural sources. In some embodiments, the agent may be selected and/or prepared to bind coarse particles, fine particles, and/or ultrafine particles. For example, a porous agent with relatively small pores may be used to enhance binding of ultrafine particles, and a porous agent with relatively large pores may be used to enhance binding of particles that include coarse particles. Additionally or alternatively, a porous agent may have a pore size selected to support its ability to provide a physical barrier between one or more air pollutants and internal nasal surfaces.

In some embodiments, the surface of the agent—optionally including the inner pore surface of porous agents—is functionalized to bind air pollutants and/or to provide a physical barrier between one or more air pollutants and internal nasal surfaces. In some embodiments, the agent is functionalized with one or more organic moieties. In some embodiments, the agent is functionalized (e.g., via binding to silanol groups on the agent) with one or more of thiol groups, amine groups, crown ethers, quaternary alkyl amines, alkyl chains, alkoxysilanes, fluorenylmethoxycarbonyl-modified organosilanes, hydrophobic groups, mercaptopropyl groups, aminopropyl groups, hydroxypropyl groups, phenyl groups, or combinations of two or more thereof. Exemplary functionalization groups are set forth in Vallet-Regi et al., BIOMEDICAL APPLICATIONS OF MESOPOROUS CERAMICS: DRUG DELIVERY, SMART MATERIALS AND BONE TISSUE ENGINEERING (2013), which is incorporated herein by reference.

In some embodiments, the compositions have one or more of the following advantages: a reduction of the amount of solidifying agents that do not bind to air pollutants and/or that do not support the composition's ability to provide a physical barrier between one or more air pollutants and internal nasal surfaces; low or no toxicity potential; suitability for relatively high amounts of air pollutant binding and/or blocking; control over air pollutant binding and/or blocking, e.g., by change in pore size and shape of the agent and by functionalization of the internal or external interfaces, or both; no suspension-related problems such as Ostwald ripening or concerns with regard to uniformity (i.e., segregation); ability to possess efficacy at variable sizes of agent particles; lipophilic or hydrophilic air pollutants, or even both, can be bound to or blocked by the composition; the composition is suitable for allergic patients, e.g., because the composition can lack agents that induce an allergic response; a simple and economical manufacturing process; the composition can be thixotropic and spreadable (and thus remove concerns related to propelling the composition into a specific site of the nasal cavity and to head position, spray angle, and plume geometry); and maximal nasal mucosal surface can be covered.

The agent may be comprised of any material suitable for use in a nasal pharmaceutical composition and onto which air pollutants can bind in accordance with the disclosure herein or which can provide a physical barrier between one or more air pollutants and internal nasal surfaces. Non-limiting examples of suitable materials are provided below.

Nonporous Agents

In some embodiments, the composition comprises a nonporous agent that binds to one or more air pollutants and/or that provides a physical barrier between one or more air pollutants and internal nasal surfaces. In some embodiments, the nonporous agent comprises silicon dioxide (such as colloidal silicon dioxide), lime, limestone, polysaccharide-based materials (e.g., materials derived from chitin, chitosan, and/or starch), and combinations of two or more thereof. In some embodiments, the nonporous agent comprises fumed silicon dioxide, such as AEROSIL® 200 (hydrophilic fumed silica with a surface area of about 175 to about 225 m2/g, such as about 200 m2/g, from Evonik Industries, Corp.) and/or CAB-O-SIL® M-5 (untreated fumed silica with a surface area of about 200 m2/g, from Cabot Corp.).

In some embodiments, the nonporous agent comprises nonporous particles. Some embodiments comprise spray dried particles. In some embodiments, the particles are in a dry powder form. In some embodiments, the particles are in a granulated form, such as AEROSIL® 300 (hydrophilic fumed silica with a surface area of about 270 to about 330 m2/g, such as about 300 m2/g, from Evonik Industries, Corp.). In some embodiments, the particles are functionalized. In some embodiments, the particles have a surface area of at least about 200 m2/g, such as about 200 m2/g, about 250, about 300 m2/g, about 350 m2/g, about 400 m2/g, about 450 m2/g, or about 500 m2/g. In some embodiments, the particles have a surface area of at least 200 m2/g, such as 200 m2/g, 250, 300 m2/g, 350 m2/g, 400 m2/g, 450 m2/g, or 500 m2/g.

In some embodiments, the nonporous agent binds to one or more air pollutants. In some embodiments, the nonporous agent provides a physical barrier between one or more air pollutants and internal nasal surfaces. In some embodiments, the nonporous agent binds to one or more air pollutants and provides a physical barrier between one or more air pollutants and internal nasal surfaces.

Porous Agents

Additionally or alternatively, in some embodiments the composition comprises a porous agent that binds to one or more air pollutants and/or that provides a physical barrier between one or more air pollutants and internal nasal surfaces. In some embodiments, the porous agent comprises an inorganic porous material, such as colloidal silicon dioxide, micro-porous silicon dioxide, meso-porous silicon dioxide, macro-porous silicon dioxide, polyorganosiloxanes, pharmaceutical clays, silicon dioxide nanotubes, silicon dioxide gel, magnesium alumosilicate (e.g., VEEGUM® from Vanderbilt Minerals, LLC), activated carbon, anhydrous calcium phosphate, calcium carbonate, alumina, and combinations of any two or more thereof. Exemplary inorganic porous materials include porous silicon dioxide commercially available under the SYLOID® brand from W.R. Grace & Co. (e.g., SYLOID® 244FP, 72FP, XDP6035, XDP3050, XDP3150, AL-1FP, and combinations of any two or more thereof), porous silicon dioxide available under the AEROPERL® brand from Evonik Industries, Corp. (e.g., AEROPERL® 300, which has a surface area of about 260 to 320 m2/g (such as about 300 m2/g), a pore volume of about 1.5 to 1.9 ml/g, and an average particle size of about 20 to about 60 μm), silicon dioxide PARTECK® SLC from EMD Millipore, NEUSILIN® (a synthetic, amorphous form of magnesium aluminometasilicate) from Fuji Chemical Industry, Zeolite Socony Mobil-5, Mobil Composition of Matter No. 41, SBA-15, FDU-11, OMS-7, OMS-Lemon-7, and IITM-56. In some embodiments, the porous agent comprises silicon-based powders, which may be hydrophobic or hydrophilic, e.g., depending on groups chemically bonded to their surfaces.

Additionally or alternatively, in some embodiments the porous agent comprises an organic-inorganic hybrid, such as metal-organic frameworks (MOFs). Exemplary hybrid materials can be formed by self-assembly of polydentate bridging ligands and metal connecting points.

Additionally or alternatively, in some embodiments the porous agent comprises organic polymers, such as microporous organic polymers, polystyrene, cellulose, and/or poly(methyl methacrylate). In some embodiments, microporous organic polymers are formed by carbon-carbon coupling reactions and comprised of non-metallic elements such as carbon, hydrogen, oxygen, nitrogen, and/or boron. In some embodiments, organic polymers are produced by emulsion polymerization and hypercrosslinking followed by chemical etching of sacrificial SiO2 cores. In some embodiments, networks of organic polymers are constructed from small organic building blocks.

Additionally or alternatively, in some embodiments the porous agent comprises porous materials based on complexing agents, such as an ion exchange resin (e.g., crosslinked polystyrene) or an adsorbent (e.g., β-cyclodextrin-based porous silicon dioxide, α-cyclodextrin-based porous silicon dioxide, hydroxypropyl-β-cyclodextrin-based porous silicon dioxide, and porous materials based on other adsorbent resins).

Additionally or alternatively, in some embodiments the porous agent comprises a material with pores with highly variable sizes and irregular shapes, such as an agent comprising polylactide and/or polylactic acid. In some embodiments, the polylactide comprises polylactides available under the RESOMER® brand available from Sigma-Aldrich (e.g., RESOMER® 202H (which has a molecular weight of about 10,000 to about 18,000 Da; a viscosity of about 0.16 to about 0.24 dl/g; a Tg of about 44 to about 48° C.; and free carboxylic acid end groups) and RESOMER® 202S (which has a molecular weight of about 10,000 to about 18,000 Da; a viscosity of about 0.16 to about 0.24 dl/g; a Tg of about 38 to about 42° C.; and ester terminated end groups)), and combinations of two or more thereof. In some embodiments, the porous agent comprises polysaccharides, such as chitosan (e.g., chitosan with 95% degree of deacylation and a viscosity of about 200 mPa). An exemplary chitosan in this regard is CHITOSCIENCE® Chitosan 95/200 from Heppe Medical Chitosan GmbH. In some embodiments, the porous agent comprises peptides and/or proteins, such as gelatin (e.g., gelatin with bloom grades F15, F20, F25, or combinations of two or more thereof). In some embodiments, the gelatin comprises a fish-based pharmaceutical grade gelatin, e.g., from Lapi Gelatine.

For any type of porous agent, the porous agent may comprise pores with a longest diameter in any dimension of 2 nm or less (e.g., the porous agent comprises micro-porous materials). In some embodiments, the porous agent comprises pores with a longest diameter of from about 2 nm to about 50 nm, such as from 20 nm to 50 nm (e.g., the porous agent comprises meso-porous materials). In some embodiments, the porous agent comprises pores with a longest diameter of 50 nm or more (e.g., the porous agent comprises macro-porous materials). In some embodiments, the porous agent comprises pores with a longest diameter of from about 2 nm to about 20 nm, such as from 2 nm to 20 nm. In some embodiments, at least about 90% of the pores have a diameter of from about 5 nm to about 6 nm, about 5 nm to about 7.5 nm, about 5.5 nm to about 7 nm, about 6 nm to about 7.5 nm, or about 6 nm to about 8 nm. In some embodiments, at least about 90% of the pores have a diameter of from 5 nm to 6 nm, 5 nm to 7.5 nm, 5.5 nm to 7 nm, 6 nm to 7.5 nm, or 6 nm to 8 nm. In some embodiments, the pores have an average volume of from about 0.5 ml/g to about 2 ml/g, such as about 1 ml/g, about 1.6 ml/g, or about 1.75 ml/g. In some embodiments, the pores have an average volume of from 0.5 ml/g to 2 ml/g, such as 1 ml/g, 1.6 ml/g, or 1.75 ml/g. In some embodiments, the pores have an average volume of greater than about 0.9 ml/g, or greater than 0.9 ml/g. In some embodiments, the pores have a surface area of about 300 $m^2/g$ or greater, or from about 320 to about 1000 $m^2/g$. In some embodiments, the pores have a surface area of 300 $m^2/g$ or greater, or from 320 to 1000 $m^2/g$. In some embodiments, the pores have a surface area of 1000 $m^2/g$ or greater.

For any type of porous agent, the porous agent may have pores of any type of pore structure. For example, the pore cross-section may have a regular geometric shape, such as a circular, elliptical, rectangular, or square shape, or an irregular shape. In some embodiments, the porous agent comprises pores with a regular shape and pores with an irregular shape. In some embodiments the porous agent additionally or alternatively comprises pores with a connected pore structure, pores with an unconnected pore structure, or both. In some embodiments the porous agent additionally or alternatively comprises ordered arrays of pores, disordered arrays of pores, or both.

In some embodiments, the porous agent comprises porous particles (e.g., ordered mesoporous silicon dioxide, SYLOID® particles such as AL-1FP, 72FP, 244FP, XDP3050, XDP3150, or XDP6035 (also known as SIL-SOL™ 6035)). Some embodiments comprises spray dried particles. In some embodiments, the particles are in a dry powder form. In some embodiments, the particles are in a granulated form.

For reference, approximate specifications of various SYLOID® particles are as follows:

| Property | AL-1FP | 72FP | 244FP | XDP3050 | XDP3150 | XDP6035 |
|---|---|---|---|---|---|---|
| SiO$_2$ (dried basis) (%) | 99.6 | 99.6 | 99.6 | 99.6 | 99.6 | 99.8 |
| Average particle size (μm) | 7.5 | 6.0 | 3.5 | 50 | 150 | 37 |
| Oil adsorption (lbs/100 lbs) | 80 | 220 | 300 | 300 | 300 | |
| Bulk density (g/l) | 566 | 112 | 70 | 275 | 275 | 420 |
| Average pore volume (cc/gm) | 0.4 | 1.2 | 1.6 | 1.7 | 1.7 | 0.98 |

In some embodiments, the porous agent binds to one or more air pollutants. In some embodiments, the porous agent provides a physical barrier between one or more air pollutants and internal nasal surfaces. In some embodiments, the porous agent binds to one or more air pollutants and provides a physical barrier between one or more air pollutants and internal nasal surfaces.

Immunomodulatory Agents

In some embodiments, a nasal composition as described herein comprises one or more immunomodulatory agents. As used herein, "an immunomodulatory agent" is any biological or synthetic substance that can stimulate or suppress an immune response. An immunomodulatory agent may stimulate or suppress an immune response to a single antigen, or may have a non-specific effect, causing altered host immune reactivity to many different antigens.

In specific embodiments, the immunomodulatory agent is an immunosuppressive agent. As used herein, "an immunosuppressive agent" is any biological or synthetic substance that suppresses an immune response. In the context of the methods and compositions described herein, an immunosuppressive agent may suppress an immune response to one or more air pollutants and thereby reduce inflammation, allergic response, and risk of asthma, for example. Immune responses depend on activation, proliferation, and maturation of the B and T cells of the adaptive immune system, or activation of phagocytes and natural killer cells of the innate immune system. These immune responses are initiated, regulated, and maintained by numerous cell signaling molecules whose receptors are expressed on immune cells. Immunosuppressive agents may target these signaling molecules or their receptors to suppress immune responses.

Examples of immunosuppressive agents include, but are not limited to, tacrolimus, mycophenolate sodium, corticosteroids, glucocorticoids, agonists or antagonists of immune system activation, proliferation, or maturation pathways such as the JNK (Jun amino-terminal kinases), MAPK (Mitogen-activated protein kinase), ERK (extracellular signal-regulated kinases), NF kappa B (nuclear factor kappa-light-chain-enhancer of activated B cells) pathway; agonists or antagonists of monocyte, neutrophil, or macrophage response pathways, STATE inhibitors, agonists or antagonists of natural killer cell and natural killer T cells, agonists or antagonists of calcineurin (including partial agonists, inverse agonists, and allosteric modulators), agonists or antagonists of chemokines or chemokine receptors, agonists or antagonists of cytokines and cytokine receptors. Examples of immunosuppressive agents also include, but are not limited to, antibodies against chemokines, chemokine receptor, cytokines or cytokine receptors.

In specific embodiments, a nasal composition as described herein comprises, as one or more immunosuppressive agents, one or more antibodies against one or more cytokines, such as antibodies against IL-2 (e.g., basiliximab/Simulect®, declizumab/Zenapax®, Tacrolimus/Prograf/FK506, Sirolimus/Rapamune®), IL-4 (e.g., IL-4 (Pascolizumab®), IL-5 (Mepolizumab®, Reslizumab®, Benralizumab®), IL-13 (Lebrikizumab®)), or TNFα. In some embodiments, a nasal composition as described herein comprises, as one or more immunosuppressive agents, one or more Th2 cytokine inhibitors (e.g., Suplatast tosylate). In some embodiments, a nasal composition as described herein comprises, as one or more immunosuppressive agents, one or more recombinant anti-IgE antibodies (e.g., Omalizumab®). In some embodiments, a nasal composition as described herein comprises, as one or more immunosuppressive agents, one or more glucocorticoids, antibiotics (such as daptomycin, dactinomycin, anthracyclines, mitomycin C, bleomycin, mithramycin), polysaccharides (such as beta-glucan), antihistamines (e.g., Bilastine®, Rupatadine®), or Rapamycin. In some embodiments, however, the composition does not include an immunomodulatory agent.

The one or more immunosuppressive agents may be present in an amount effective to achieve the intended effect, such as to reduce an immune response to one or more air pollutants, reduce inflammation, reduce allergic response, and/or reduce risk of asthma. In some embodiments, the immunosuppressive agent is present at a concentration of from about 0.001% to about 5% by weight of the composition. In some embodiments, the immunosuppressive agent is present at a concentration of from about 0.01% to about 2%, from about 0.1% to about 1%, or from about 1% to about 5%, all by weight of the composition.

Additional Components

As noted above, the nasal compositions described herein may comprise, in addition to an agent that binds to one or more air pollutants, a vehicle and, optionally, a viscosity-regulating (e.g., gelling) agent. In some embodiments, the other components may support the composition's ability to provide a physical barrier between one or more air pollutants and internal nasal surfaces.

The vehicle may be any vehicle suitable as a vehicle for a nasal pharmaceutical composition. In some embodiments, the vehicle for the agent is a hydrophilic vehicle. In some embodiments, the vehicle is a lipophilic or partly lipophilic vehicle, such as a vehicle comprising one or more fats, oils, waxes, phospholipids, steroids (e.g., cholesterol), sphingolipids, ceramides, sphingosines, prostaglandins, and/or fat-oil vitamins. In some embodiments, the vehicle comprises an oil or a mixture of oils, such as vegetable oil, castor oil, hydrogenated castor oil, soybean oil, sesame oil, or peanut oil; fatty acid esters, such as ethyl- and oleyl-oleate, isopropylmyristate; medium chain triglycerides; glycerol esters of fatty acids; polyethylene glycol; phospholipids; white soft paraffin; or combinations of any two or more thereof.

The vehicle may be present in any suitable amount, such as an amount effective to provide desired properties for nasal administration, desired physical properties, desired binding properties, etc. In some embodiments, the composition comprises a vehicle in an amount of from about 15% to about 98% by weight, about 30 to about 98% by weight, about 50% to about 95% by weight, about 75% to about 95% by weight, about 80%, or about 90% by weight, based on the total weight of the composition. In some embodiments, the composition comprises a vehicle in an amount of from 15% to 98% by weight, 30 to 98% by weight, 50% to 95% by weight, 75% to 95% by weight, 80%, or 90% by weight, based on the total weight of the composition.

The viscosity-regulating agent, if present, may be any viscosity-regulating agent suitable for use as a viscosity-regulating agent in a nasal pharmaceutical composition. In some embodiments, the viscosity-regulating agent comprises silicon dioxide (e.g., porous or nonporous silicon dioxide). In some embodiments, the viscosity-regulating agent comprises cellulose, cellulose-containing substances, polysaccharides, carbomers, polyvinyl alcohol, povidone, cetyl alcohols, stearic acid, beeswax, petrolatum, triglycerides, lanolin, or combinations of any two or more thereof. In some embodiments, the viscosity-regulating agent comprises colloidal silicon dioxide (e.g., AEROSIL® 200 (Evonik) and/or CAB-O-SIL® M5 (Cabot)). In some embodiments, the viscosity-regulating agent comprises synthetic silica, such as SYLODENT® (precipitated silica with a compacted bulk density of about 110 kg/m$^3$, a specific surface area of about 190 m$^2$/g, and an average particle size of about 18 µm) or SYLOBLANC® silicas (porous silica gel with a pore volume of about 1.6 ml/g and an average particle size of about 3 µm) from W.R. Grace & Co. In some embodiments, the viscosity-regulating agent comprises hydrophilic fumed silicon dioxide, such as AEROSIL® 200, and/or lipophilic silicon dioxide, such as AEROSIL® R972 (which is fumed silica treated with dimethyldichlorosilane, and which has a surface area of about 90 to about 130 m$^2$/g). Without being bound by theory, it is believed that hydrophilic fumed silicon dioxide can be used to prepare a thixotropic gel composition with a high temperature stability as compared to a comparable gel produced with other viscosity-regulating agents.

The viscosity-regulating agent, if present, may be present in an amount effective to adjust the viscosity of the composition to the desired level. In some embodiments, the composition comprises from about 0.5 to about 20% by weight, about 0.5 to about 10% by weight, about 0.5 to about 7% by weight, about 1 to about 4% by weight, about 4% by weight, or about 2% by weight viscosity-regulating agent, based on the total weight of the composition. In some embodiments, the composition comprises from 0.5 to 20% by weight, 0.5 to 10% by weight, 0.5 to 7% by weight, 1 to 4% by weight, 4% by weight, or 2% by weight viscosity-regulating agent, based on the total weight of the composition.

In some embodiments, the composition has a viscosity as measured by a rotating viscometer of about 2,000 mPa·sec to about 10,000 mPa·sec, such as about 2,000 mPa·sec, about 3,000 mPa·sec, about 4,000 mPa·sec, about 5,000 mPa·sec, about 6,000 mPa·sec, about 7,000 mPa·sec, about 8,000 mPa·sec, about 9,000 mPa·sec, or about 10,000 mPa·sec. In some embodiments, the composition has a viscosity as measured by a rotating viscometer of 2,000 mPa·sec to 10,000 mPa·sec, such as 2,000 mPa·sec, 3,000 mPa·sec, 4,000 mPa·sec, 5,000 mPa·sec, 6,000 mPa·sec, 7,000 mPa·sec, 8,000 mPa·sec, 9,000 mPa·sec, or 10,000 mPa·sec.

In some embodiments, the agent functions as the only viscosity-regulating agent in the composition. Thus, in some embodiments the composition does not include a viscosity-regulating agent other than the agent(s). In some embodiments, a non-porous agent (e.g., a fumed silia such as AEROSIL® 200) is more effective as a gelling agent than a porous agent (e.g., a porous silicon dioxide such as SYLOID® 244). Thus, in some embodiments the amount of agent is adjusted to achieve the desired viscosity and/or another viscosity-regulating agent is used. For example, when the agent comprises a porous silica such as SYLODENT® or SYLOBLANC®, an additional viscosity-regulating agent may be used, including an additional silicon dioxide compound.

In some embodiments, the agent has isolated, germinal, and/or vicinal silanol groups. In some embodiments, the silanol groups may interact with the air pollutant(s) and thereby contribute to the efficacy of the composition. In some embodiments, one or more of the silanol groups are functionalized, as discussed above. In some embodiments, silanol groups are functionalized to provide selective adsorption of target molecules, e.g., target air pollutants.

The composition may or may not contain other components suitable for use in a nasal pharmaceutical composition. For example, in some embodiments, the composition may independently comprise one or more of a solubilization agent; a cosolvent; a charge modifying agent; a pH control agent; an osmotic adjusting agent; a degradative enzyme inhibitor; an antioxidant; a stabilizer; an emulsifying agent; a wetting agent; a suspending agent; a surfactant; a pharmaceutical active agent; or an adhesive. In some embodiments, the composition independently does not contain one or more of (i.e., one or more of the following are not present in the composition) a solubilization agent; a cosolvent, a charge modifying agent; a pH control agent; an osmotic adjusting agent; a degradative enzyme inhibitor; an antioxidant; a stabilizer; a membrane penetration-enhancing agent; an emulsifying agent; a wetting agent; a suspending agent; a surfactant; a pharmaceutical active agent; an adhesive; and a taste-masking agent.

In some embodiments, the composition comprises one or more of camphor, eucalyptus oil, menthol, saccharin, succinic acid, zinc acetate, polyethyleneglycol, aroma, polysorbate 80, hydroxypropylmethylcellulose, disodium succinate, pyroglutamic acid, zinc edetate, zinc, mint oil, bentonite, xanthan, glycerol, glycerol monostearate, potassium phosphate, dipotassium phosphate, sesame oil, water, tocopherol, mint oil, and preservatives. In some embodiments, the composition does not contain one or more of (i.e., one or more of the following are not present in the composition): camphor, eucalyptus oil, menthol, saccharin, succinic acid, zinc acetate, polyethyleneglycol, aroma, polysorbate 80, hydroxypropylmethylcellulose, disodium succinate, pyroglutamic acid, zinc edetate, zinc, mint oil, bentonite, xanthan, glycerol, glycerol monostearate, potassium phosphate, dipotassium phosphate, sesame oil, water, tocopherol, mint oil, and preservatives.

The optional components discussed here, if present, may be present in an amount effective to exhibit their intended functions and/or to confer desired properties to the composition.

In some embodiments, the agent that binds to one or more air pollutants is the only agent in the composition.

In some embodiments, the composition does not contain a pharmaceutically active agent. Additionally or alternatively, in some embodiments the composition does not contain camphor. Additionally or alternatively, in some embodiments the composition does not contain eucalyptus oil. Additionally or alternatively, in some embodiments the composition does not contain menthol. Additionally or alternatively, in some embodiments the composition does not contain saccharin. Additionally or alternatively, in some embodiments the composition does not contain succinic acid. Additionally or alternatively, in some embodiments the composition does not contain zinc acetate. Additionally or alternatively, in some embodiments the composition does not contain polyethyleneglycol. Additionally or alternatively, in some embodiments the composition does not contain polysorbate 80. Additionally or alternatively, in some embodiments the composition does not contain hydroxypropylmethylcellulose. Additionally or alternatively, in some embodiments the composition does not contain disodium succinate. Additionally or alternatively, in some embodiments the composition does not contain pyroglutamic acid. Additionally or alternatively, in some embodiments the composition does not contain zinc edetate. Additionally or alternatively, in some embodiments the composition does not contain polyethyleneglycol. Additionally or alternatively, in some embodiments the composition does not contain aroma. Additionally or alternatively, in some embodiments the composition does not contain polysorbate 80. Additionally or alternatively, in some embodiments the composition does not contain hydroxypropylmethylcellulose. Additionally or alternatively, in some embodiments the composition does not contain disodium succinate. Additionally or alternatively, in some embodiments the composition does not contain pyroglutamic acid. Additionally or alternatively, in some embodiments the composition does not contain zinc edetate. Additionally or alternatively, in some embodiments the composition does not contain zinc. Additionally or alternatively, in some embodiments the composition does not contain mint oil. Additionally or alternatively, in some embodiments the composition does not contain bentonite. Additionally or alternatively, in some embodiments the composition does not contain xanthan. Additionally or alternatively, in some embodiments the composition does not contain glycerol. Additionally or alternatively, in some embodiments the composition does not contain glycerol monostearate. Additionally or alternatively, in some embodiments the composition does not contain potassium phosphate. Additionally or alternatively, in some embodiments the composition does not contain dipotassium phosphate. Additionally or alternatively, in some embodiments the composition does not contain sesame oil. Additionally or alternatively, in some embodiments the composition does not contain water. Additionally or alternatively, in some embodiments the composition does not contain tocopherol. Additionally or alternatively, in some embodiments the composition does not contain mint oil. Additionally or alternatively, in some embodiments the composition does not contain and preservatives.

The surfactant, if present, may be any surfactant suitable for use as a surfactant in a nasal pharmaceutical composition. In some embodiments, the surfactant is selected from anionic, cationic, amphoteric, and non-ionic surfactants, including, but not limited to, lecithin, fatty acid esters of polyvalent alcohols, fatty acid esters of sorbitanes, fatty acid esters of polyoxyethylensorbitans, fatty acid esters of polyoxyethylene, fatty acid esters of sucrose, fatty acid esters of polyglycerol, oleoyl polyoxylglycerides (e.g., apricot kernel oil PEG-6-esters), oleoyl macrogolglycerides, and/or humectants such as sorbitol, glycerine, polyethylene glycol, macrogol glycerol fatty acid ester, and combinations of any two or more thereof. In some embodiments, the surfactant comprises an oleoyl macrogolglyceride (such as LABRAFIL® M 1944 CS (Gattefosse, Saint-Priest, France)) or a mixture of oleoyl macrogolglycerides.

The surfactant, if present, may be present in an amount effective to exert surfactant properties. In some embodiments, the composition comprises from about 1 to about 20% by weight, about 1 to about 10% by weight, about 1 to about 5% by weight, about 4% by weight, or about 2% by weight surfactant, based on the total weight of the composition. In some embodiments, the composition comprises from 1 to 20% by weight, 1 to 10% by weight, 1 to 5% by weight, 4% by weight, or 2% by weight surfactant, based on the total weight of the composition.

Exemplary Compositions

In some exemplary embodiments, the composition comprises (a) from about 0.5% to about 50% w/w of an agent that binds to one or more air pollutants (such as one or more of any described herein), based on the weight of the composition; (b) from about 50% to about 90% w/w of castor oil, based on the weight of the composition; and (c) from about 0.5% to about 20% w/w of apricot kernel oil PEG-6-esters (such as one or more of those described herein, such as oleoyl polyoxyl-6 glycerides, e.g., Labrafil®), based on the weight of the composition. In some exemplary embodiments, the composition comprises (a) from about 0.5% to about 50% w/w of an agent that binds to one or more air pollutants (such as one or more of any described herein), based on the weight of the composition; (b) from about 50% to about 95% w/w of castor oil, based on the weight of the composition; and (c) from about 0.5% to about 20% w/w of apricot kernel oil PEG-6-esters (such as one or more of those described herein), based on the weight of the composition.

In some exemplary embodiments, the composition comprises (a) from about 0.5% to about 50% w/w of an agent that binds to one or more air pollutants (such as one or more of any described herein), based on the weight of the composition; (b) from about 50% to about 90% w/w of castor oil, based on the weight of the composition; and (c) from about 2% to about 6% w/w of apricot kernel oil PEG-6-esters (such as one or more of those described herein, such as oleoyl polyoxyl-6 glycerides, e.g., Labrafil®), based on the weight of the composition. In some exemplary embodiments, the composition comprises (a) from about 0.5% to about 50% w/w of an agent that binds to one or more air pollutants (such as one or more of any described herein), based on the weight of the composition; (b) from about 50% to about 95% w/w of castor oil, based on the weight of the composition; and (c) from about 2% to about 6% w/w of apricot kernel oil PEG-6-esters (such as one or more of those described herein), based on the weight of the composition.

In some exemplary embodiments, the composition comprises (a) from about 6% to about 11% w/w of an agent that binds to one or more air pollutants (such as one or more of any described herein), based on the weight of the composition; and (b) from about 70% to about 80% w/w of castor oil, based on the weight of the composition. In some exemplary embodiments, the composition comprises from about 0.5% to about 10% of a viscosity regulating agent (such as one or more of any described herein), based on the weight of the composition. In some exemplary embodiments, the composition comprises from about 0.5% to about 20% of a viscosity regulating agent (such as one or more of any described herein), based on the weight of the composition.

In some exemplary embodiments, the composition comprises (a) about 8% w/w of an agent that binds to one or more air pollutants (such as one or more of any described herein), based on the weight of the composition; (b) about 80% w/w of castor oil, based on the weight of the composition; and (c) about 10% w/w of apricot kernel oil PEG-6-esters (such as one or more of those described herein, such as oleoyl polyoxyl-6 glycerides, e.g., Labrafil®), based on the weight of the composition.

In some exemplary embodiments, the compositions comprise (a) a nasal gel containing from about 1% to about 50% w/w of an agent that binds to one or more air pollutants (such as one or more of any described herein), based on the weight of the composition and (b) additional agents up to 100% w/w of the weight of the composition (such as one or more of any described herein).

In any of these embodiments, the agent that binds to one or more air pollutants may be a silicon dioxide product such as one or more of AEROSIL® 200, SYLOID® AL-1FP, or SYLOID® 244 FP. Independently, in any of these embodiments, the apricot kernel oil PEG-6-esters may be provided as LABRAFIL®.

In one specific exemplary embodiment, the composition comprises 8.7% w/w colloidal hydrated silica (e.g., Syloid® 244 FP), 4.0% w/w oleoyl polyoxyl-6 glycerides (e.g., Labrafil®), and 87.3% w/w castor oil. (This formulation may be sold under the trademark Nascum®-Plus gel.) Further specific exemplary formulations are set forth in the tables below:

|  | Composition 1 % w/w | Composition 2 % w/w | Composition 3 % w/w |
| --- | --- | --- | --- |
| Castor Oil | 92% | 91% | 91% |
| oleoyl polyoxyl-6 glycerides (e.g., Labrafil®) | 4% | 4% | 4% |
| Colloidal Hydrated Silica Component |  | 5% (SYLOID® AL-1FP) | 5% (SYLOID® 244 FP) |
| Colloidal Silicon Dioxide Component | 4% (AEROSIL® 200) |  |  |

|  | Composition 4 % w/w | Composition 5 % w/w | Composition 6 % w/w |
| --- | --- | --- | --- |
| Castor Oil | 81% | 66.0% | 56.0% |
| oleoyl polyoxyl-6 glycerides (e.g., Labrafil®) | 4.0% | 4.0% | 4.0% |
| Colloidal Hydrated Silica Component | 15.0% (SYLOID® AL-1FP) | 30.0% (SYLOID® AL-1FP) | 40.0% (SYLOID® AL-1FP) |
| Colloidal Silicon Dioxide Component |  |  |  |

|  | Composition 7 % w/w | Composition 8 % w/w | Composition 9 % w/w |
| --- | --- | --- | --- |
| Castor Oil | 46% | 64.0% | 63.0% |
| oleoyl polyoxyl-6 glycerides (e.g., Labrafil®) | 4.0% | 4.0% | 4.0% |
| Colloidal Hydrated Silica Component | 50.0% (SYLOID® AL-1FP) | 30.0% (SYLOID® AL-1FP) | 30.0% (SYLOID® AL-1FP) |
| Colloidal Silicon Dioxide Component |  | 3% (AEROSIL® 200) | 3% (AEROSIL® 200) |

|  | Composition 10 % w/w | Composition 11 % w/w | Composition 12 % w/w |
| --- | --- | --- | --- |
| Castor Oil | 72% | 68.0% | 61.0% |
| oleoyl polyoxyl-6 glycerides (e.g., Labrafil®) | 4.0% | 4.0% | 4.0% |
| Colloidal Hydrated Silica Component | 20.0% (SYLOID® AL-1FP) | 20.0% (SYLOID® AL-1FP) | 20.0% (SYLOID® AL-1FP) |
| Colloidal Silicon Dioxide Component | 4% (AEROSIL® 200) | 8% (AEROSIL® 200) | 15% (AEROSIL® 200) |

-continued

|  | Composition 13<br>% w/w | Composition 14<br>% w/w | Composition 15<br>% w/w |
|---|---|---|---|
| Castor Oil | 78% | 71.0% | 76.0% |
| oleoyl polyoxyl-6 glycerides (e.g., Labrafil ®) | 4.0% | 4.0% | 4.0% |
| Colloidal Hydrated Silica Component | 10.0%<br>(SYLOID ® AL-1FP) | 10.0%<br>(SYLOID ® AL-1FP) | 5.0%<br>(SYLOID ® AL-1FP) |
| Colloidal Silicon Dioxide Component | 8%<br>(AEROSIL ® 200) | 15%<br>(AEROSIL ® 200) | 15%<br>(AEROSIL ® 200) |

|  | Composition 16<br>% w/w | Composition 17<br>% w/w | Composition 18<br>% w/w |
|---|---|---|---|
| Castor Oil | 66% | 69.0% | 79.0% |
| oleoyl polyoxyl-6 glycerides (e.g., Labrafil ®) | 4.0% | 4.0% | 4.0% |
| Colloidal Hydrated Silica Component | 15.0%<br>(SYLOID ® AL-1FP) | 15.0%<br>(SYLOID ® AL-1FP) | 5.0%<br>(SYLOID ® AL-1FP) |
| Colloidal Silicon Dioxide Component | 15%<br>(AEROSIL ® 200) | 12%<br>(AEROSIL ® 200) | 12%<br>(AEROSIL ® 200) |

|  | Composition 19<br>% w/w | Composition 20<br>% w/w | Composition 21<br>% w/w |
|---|---|---|---|
| Castor Oil | 89% | 88.2% | 87.5% |
| oleoyl polyoxyl-6 glycerides (e.g., Labrafil ®) | 4.0% | 4.0% | 4.0% |
| Colloidal Hydrated Silica Component | 6.9%<br>(SYLOID ® 244FP) | 7.8%<br>(SYLOID ® 244FP) | 8.5%<br>(SYLOID ® 244FP) |

|  | Composition 22<br>% w/w | Composition 23<br>% w/w | Composition 24<br>% w/w |
|---|---|---|---|
| Castor Oil | 92.0% | 91.0% | 90.0% |
| oleoyl polyoxyl-6 glycerides (e.g., Labrafil ®) | 4.0% | 4.0% | 4.0% |
| Precipitated Silica Component | 1.0%<br>(SYLODENT ® SM 880 T) | 2.0%<br>(SYLODENT ® SM 880 T) | 3.0%<br>(SYLOID ® AL-1FP) |
| Colloidal Silicon Dioxide Component | 3%<br>(AEROSIL ® 200) | 3%<br>(AEROSIL ® 200) | 3%<br>(AEROSIL ® 200) |

|  | Composition 25<br>% w/w | Composition 26<br>% w/w | Composition 27<br>% w/w |
|---|---|---|---|
| Castor Oil | 89% | 92.5% | 92.0% |
| oleoyl polyoxyl-6 glycerides (e.g., Labrafil ®) | 4.0% | 4.0% | 4.0% |
| Precipitated Silica Component | 4.0%<br>(SYLODENT ® SM 880 T) | 0.5%<br>(SYLOBLANC ® 34) | 1.0%<br>(SYLOBLANC ® 34) |
| Colloidal Silicon Dioxide Component | 3%<br>(AEROSIL ® 200) | 3%<br>(AEROSIL ® 200) | 3%<br>(AEROSIL ® 200) |

-continued

|  | Composition 28 % w/w | Composition 29 % w/w | Composition 30 % w/w | Composition 31 % w/w |
|---|---|---|---|---|
| Castor Oil | 91.5% | 91.0% | 90.0% | 89.2% |
| oleoyl polyoxyl-6 glycerides (e.g., Labrafil ®) | 4.0% | 4.0% | 4.0% | 4.0% |
| Precipitated Silica Component | 1.5% (SYLOBLANC ® 34) | 2.0% (SYLOBLANC ® 34) | 3.0% (SYLOBLANC ® 34) | 2.0% (SYLOBLANC ® 34) |
| Colloidal Silicon Dioxide Component | 3% (AEROSIL ® 200) | 3% (AEROSIL ® 200) | 3% (AEROSIL ® 200) | 4.8% (AEROSIL ® 200) |

Air Pollutants

"Air pollutants" as used herein refers to potentially harmful substances in the air, as may arise from anthropogenic and/or natural sources. Air pollutants can include one or both of primary air pollutants and secondary air pollutants. Primary air pollutants are emitted into the atmosphere from natural sources (e.g., sea salt, naturally suspended dust, pollen, volcanic ash) and/or anthropogenic sources (e.g., fuel combustion in thermal power generation, incineration, agriculture, domestic heating for households such as by burning biomass or fossil fuels, fuel combustion for vehicles, vehicle and road wear, and other types of anthropogenic dust). Secondary air pollutants are formed in the atmosphere through chemical and photochemical reactions involving primary air pollutants (e.g., from oxidation and transformation of primary emissions).

Examples of specific air pollutants that may be bound or blocked by the agents described herein include fly ash, volcanic ash, soil particles, sea salt, dust, soot, dessicated cellular debris, spores, pollen, bacteria, combustion products, sulfur oxides (e.g., sulfur dioxide and/or $H_2SO_4$), nitrogen oxides (e.g., nitrogen monoxide and/or nitrogen dioxide), carbon monoxide, volatile organic compounds (VOCs) (e.g., methane and/or non-methane VOCs such as toluene, xylene, and/or 1,3-butanediene), ozone (e.g., tropospheric ozone), hydrocarbons (e.g., polycyclic aromatic hydrocarbons, such as benzopyrene (e.g., benzo[a]pyrene and/or benzo[e]pyrene)), aldehydes, nitrates (e.g., peroxylacyl nitrates), persistent free radicals, heavy metals, toxic metals (e.g., lead and/or mercury), trace elements (e.g., Sb, Zn, Co, Ni, As, Pt, and/or V), crystal materials, magnetite, chlorofluorocarbons, ammonia, odor compounds (e.g., from garbage, sewage, and/or industrial processes), radioactive substances (e.g., from nuclear explosions, nuclear events, explosives, and/or natural processes such as the radioactive decay of radon), vapor condensation products, and refractory metals (e.g., added to or naturally present in fuels). Air pollutants also may include non-physiological amounts of oxygen, nitrogen, carbon dioxide, and water (e.g., amounts that pose a risk for human health).

In some embodiments, the composition or agent binds or provides a barrier against air pollutants that are in gas or vapour form. Without being bound by theory, it is believed that gaseous air pollutants are readily taken into a subject's respiratory system, where they may be deposited in the upper respiratory tract (e.g., if the pollutant is water soluble) or penetrate into the lungs.

In some embodiments, the composition or agent or composition binds or blocks air pollutants in particulate form. Such particulate air pollutants can comprise materials in solid or liquid phase suspended in the atmosphere. Particulate air pollutants can have a range of sizes. FIG. 1 shows size ranges associated with some air pollutants.

Some embodiments comprise an agent that binds particulate air components have an aerodynamic diameter of about 10 μm or less, less than about 2.5 μm, or less than about 0.1 μm. Some embodiments comprise an agent that binds particles having an aerodynamic diameter of 10 μm or less, less than 2.5 μm, or less than 0.1 μm. Some embodiments comprise an agent that binds particles with an aerodynamic diameter of from about 2.5 μm to about 10 μm, such as from 2.5 μm to 10 μm. Some embodiments comprise an agent that binds particles having an aerodynamic diameter of less than about 2.5 μm, such as less than 2.5 μm. Some embodiments comprise an agent that binds particles having an aerodynamic diameter of less than about 0.1 μm, such as less than 0.1 μm. Particles with an aerodynamic diameter of from 2.5 μm and 10 μm are termed "coarse particles." Particles with an aerodynamic diameter of less than 2.5 μm are termed "fine particles." A subset of fine particles, termed "ultrafine particles," has an aerodynamic diameter of less than 0.1 μm.

In some embodiments, the compositions as described herein comprise an agent that binds particulate air pollutants having a nominal median aerodynamic diameter of about 10 μm or less, less than about 2.5 μm, or less than about 0.1 μm. Some embodiments comprise an agent that binds particles having a nominal median aerodynamic diameter 10 μm or less, less than 2.5 μm, or less than 0.1 μm. Some embodiments comprise an agent that binds particles with a nominal median aerodynamic diameter of from about 2.5 μm to about 10 μm, such as from 2.5 μm to 10 μm. Some embodiments comprise an agent that binds particles having a nominal median aerodynamic diameter of less than about 2.5 μm, such as less than 2.5 μm. Some embodiments comprise an agent that binds particles having a nominal median aerodynamic diameter of less than about 0.1 μm, such as less than 0.1 μm. The term "PM10" is used to describe particles with a median aerodynamic diameter of 10 μm or less. The term "PM2.5" is used to describe particles with a median aerodynamic diameter of less than 2.5 μm. The term "PM2.5-10" is used to describe particles with a median aerodynamic diameter of from 2.5 μm to 10 μm. The term "PM0.1" is used to describe particles with a median aerodynamic diameter of less than 0.1 μm.

Some embodiments comprise a composition or agent that binds or blocks air pollutants in both gaseous and particulate form. For example, the agent may bind air pollutants present in an aerosol that includes both finely divided condensed matter (e.g., particulate air pollutants) and a gaseous suspending medium. See, e.g., Phalen R F, "The particulate air pollution controversy," Nonlinearity Biol Toxicol Med, 2(4): 259-9 (2004). Additionally or alternatively, the composition may block air pollutants present in an aerosol that includes both finely divided condensed matter (e.g., particulate air pollutants) and a gaseous suspending medium.

Methods of Manufacturing

Also provided herein are methods of making nasal pharmaceutical compositions as described herein.

In some embodiments, a method of making a nasal pharmaceutical composition as described herein comprises mixing an agent as described herein, such as an agent that binds to one or more air pollutants, such as one or more of porous silicone dioxide and nonporous silicone dioxide, with an oil, such as any one or more of plant oils, animal oils, and mineral oils. Exemplary oils include vegetable oil, castor oil, hydrogenated castor oil, soybean oil, sesame oil, peanut oil, linalool, TRANSCUTOL® HP (purified diethylene glycol monoethyl ether EP/NF from Gattefosse), CAPRYOL™ PGMC (propylene glycol monocaprylate (type I) NF from Gattefosse), and combinations of any two or more thereof.

In some embodiments, a method of making a nasal pharmaceutical composition as described herein comprise mixing (i) an agent as described herein, such as an that binds to one or more air pollutants, such as one or more of porous silicone dioxide and nonporous silicone dioxide, (ii) a lipophilic or partly lipophilic vehicle, and (iii) a surfactant. Some embodiments comprise mixing the vehicle and the agent, and then adding and mixing the surfactant. Other embodiments comprise mixing the vehicle and the surfactant, and then adding and mixing the agent.

Methods of Using

Also provided herein are methods of using compositions as described herein, comprising intranasal delivery to a subject in need thereof. In some embodiments, an effective amount of the composition is nasally administered to a subject in need thereof, such as by applying an amount of the composition to the nasal cavity or administering an amount of the composition into the nasal cavity, to one or both nostrils. The composition may be administered from any device suitable for administering nasal compositions, such as a multi-dose device or a single-dose device.

In some embodiments, the compositions are effective at binding air pollutants for up to 2 hours post-administration, up to 3 hours post-administration, up to 4 hours post-administration, up to 5 hours post-administration, or up to 6 hours post-administration. In some embodiments, the compositions are effective for 6 hours or more.

The composition may be administered in any suitable amount, keeping in mind the volume limitations of nasal administration. In some embodiments, about 0.1 ml to about 1 ml, such as from about 0.1 ml to about 0.3 ml, about 0.15 ml to about 0.25 ml, or about 0.175 to about 0.225 ml is administered per nostril, to one or both nostrils. In some embodiments, 0.1 ml to 1 ml, such as from 0.1 ml to 0.3 ml, 0.15 ml to 0.25 ml, or 0.175 to 0.225 ml is administered per nostril, to one or both nostrils. In some embodiments, about 0.1 ml, about 0.15 ml, about 0.2 ml, about 0.25 ml, or about 0.3 ml is administered per nostril, to one or both nostrils. In some embodiments, 0.1 ml, 0.15 ml, 0.2 ml, 0.25 ml, or 0.3 ml is administered per nostril, to one or both nostrils. In some embodiments, about 0.2 ml or less is administered per nostril, to one or both nostrils. In some embodiments, 0.2 ml or less is administered per nostril, to one or both nostrils.

In some embodiments, the amount of composition administered per nostril (to one or both nostrils) comprises from about 0.001 g to about 0.3 g of agent, such as from about 0.005 g to about 0.2 g of agent, or from about 0.01 g to about 0.1 g of agent. In some embodiments, the the amount of composition administered per nostril (to one or both nostrils) comprises from 0.001 g to 0.3 g of agent, such as from 0.005 g to 0.2 g of agent, or from 0.01 g to 0.1 g of agent. In some embodiments, the amount of composition administered per nostril (to one or both nostrils) comprises about 0.001 g, about 0.004 g, about 0.005 g, about 0.01 g, about 0.02 g, about 0.03 g, about 0.04 g, about 0.05 g, about 0.09 g, or about 0.1 g of agent. In some embodiments, the amount of composition administered per nostril (to one or both nostrils) comprises 0.001 g, 0.004 g, 0.005 g, 0.01 g, 0.02 g, 0.03 g, 0.04 g, 0.05 g, 0.09 g, or 0.1 g of agent.

In some embodiments, the composition is administered once daily per nostril, to one or both nostrils. In some embodiments, the composition is administered twice daily per nostril, to one or both nostrils. In some embodiments, the composition is administered three, four, five, or six times per day per nostril, to one or both nostrils.

In some embodiments, the methods comprise administering a composition as described herein to a subject at risk of exposure to air pollutants. For example, some embodiments comprise administering a composition as described herein to a subject that resides or works in or near a metropolitan area and/or an industrial area and/or a factory. Some embodiments comprise administering a composition as described herein to a subject that is or will be a visitor to a metropolitan area and/or an industrial area and/or a factory. Some embodiments comprise administering a composition as described herein to a subject that is employed in a metropolitan area and/or an industrial area and/or a factory. Some embodiments comprise administering the composition to a subject that resides in or visits an area with more than about 50 $\mu g/m^3$ air pollutants, such as more than 50 $\mu g/m^3$ air pollutants (e.g., more than 50 $\mu g/m^3$ suspended particulates with an aerodynamic diameter smaller than 10 $\mu m$), more than 100 $\mu g/m^3$ air pollutants, more than 250 $\mu g/m^3$ air pollutants, more than 350 $\mu g/m^3$ air pollutants, or more than 430 $\mu g/m^3$ air pollutants.

Some embodiments comprise administering the composition to a subject that resides in, visits, and/or is employed in an area with an Air Quality Index (AQI) rating of moderate, unhealthy for sensitive groups, unhealthy, very unhealthy, or hazardous as defined by the United States Environmental Protection Agency (EPA). EPA AQI ratings are based on the concentration (in $\mu g/m^3$) of any of five pollutants measured over a pre-determined time period (e.g., 1 hr, 8 hrs, or 24 hrs): ground-level ozone, particulate matter, carbon monoxide, sulfur dioxide, and nitrogen dioxide, as shown in Table 1. The AQI category is defined by the pollutant with the largest AQI value.

TABLE 1

EPA Air Quality Ratings

| $O_3$ (ppb) | $O_3$ (ppb) | $PM_{2.5}$ (μg/m³) | $PM_{10}$ (μg/m³) | CO (ppm) | $SO_2$ (ppb) | $NO_2$ (ppb) | AQI | AQI |
|---|---|---|---|---|---|---|---|---|
| $C_{low}$-$C_{high}$ (avg) | $C_{low}$-$C_{high}$ (avg) | $C_{low}$-$C_{high}$ (avg) | $C_{low}$-$C_{high}$ (avg) | $C_{low}$-$C_{high}$ (avg) | $C_{low}$-$C_{high}$ (avg) | $C_{low}$-$C_{high}$ (avg) | $I_{low}$-$I_{high}$ | Category |
| 0-54 (8-hr) | — | 0.0-12.0 (24-hr) | 0-54 (24-hr) | 0.0-4.4 (8-hr) | 0-35 (1-hr) | 0-53 (1-hr) | 0-50 | Good |
| 55-70 (8-hr) | — | 12.1-35.4 (24-hr) | 55-154 (24-hr) | 4.5-9.4 (8-hr) | 36-75 (1-hr) | 54-100 (1-hr) | 51-100 | Moderate |
| 71-85 (8-hr) | 125-164 (1-hr) | 35.5-55.4 (24-hr) | 155-254 (24-hr) | 9.5-12.4 (8-hr) | 76-185 (1-hr) | 101-360 (1-hr) | 101-150 | Unhealthy for Sensitive Groups |
| 86-105 (8-hr) | 165-204 (1-hr) | 55.5-150.4 (24-hr) | 255-354 (24-hr) | 12.5-15.4 (8-hr) | 186-304 (1-hr) | 361-649 (1-hr) | 151-200 | Unhealthy |
| 106-200 (8-hr) | 205-404 (1-hr) | 150.5-250.4 (24-hr) | 355-424 (24-hr) | 15.5-30.4 (8-hr) | 305-604 (24-hr) | 650-1249 (1-hr) | 201-300 | Very Unhealthy |
| — | 405-504 (1-hr) | 250.5-350.4 (24-hr) | 425-504 (24-hr) | 30.5-40.4 (8-hr) | 605-804 (24-hr) | 1250-1649 (1-hr) | 301-400 | Hazardous |
| — | 505-604 (1-hr) | 350.5-500.4 (24-hr) | 505-604 (24-hr) | 40.5-50.4 (8-hr) | 805-1004 (24-hr) | 1650-2049 (1-hr) | 401-500 | |

Thus, some embodiments comprise administering the composition to a subject that resides in, visits, and/or is employed in an area with a AQI of more than 50, more than 100, more than 150, more than 200, more than 300, more than 400, or more than 500.

Some embodiments comprise administering the composition to a subject aged about 65 or older. In some embodiments, the subject is a female subject. In other embodiments, the subject is a male subject. In some embodiments, the subject is a diabetic subject. In some embodiments, the subject is a smoker (e.g., an individual who smokes, on average, at least one cigarette per day). Some embodiments comprise administering the composition to a subject that works in a factory. Some embodiments comprise administering the composition to a subject that has (e.g., has been diagnosed as having) hypertension and/or another cardiovascular disease. Some embodiments comprise administering the composition to a female subject during the first trimester of pregnancy, the second trimester of pregnancy, and/or the third trimester of pregnancy.

Some embodiments comprise administering a composition as described herein in one or more of January, February, March, April, May, June, July, August, September, October, November, and December. Some embodiments comprise administering the composition during summer months, e.g., June, July, and/or August.

Some risks of exposure to air pollutants are associated with air pollutants that have an aerodynamic diameter of less than 2.5 μm. Thus, some embodiments comprise administering compositions that bind or block air pollutants that have an aerodynamic diameter of less than 2.5 μm. Some risks of exposure to air pollutants are associated with air pollutants that have an aerodynamic diameter of from 2.5 μm to 10 μm. Thus, some embodiments comprise administering compositions that bind or block air pollutants that have an aerodynamic diameter of from 2.5 μm to 10 μm. Some risks of exposure to air pollutants are associated with air pollutants that have an aerodynamic diameter of 10 μm or less. Thus, some embodiments comprise administering compositions that bind or block air pollutants that have an aerodynamic diameter of 10 μm or less. Some risks of exposure to air pollutants are associated with air pollutants that have an aerodynamic diameter of more than 10 μm. Thus, some embodiments comprise administering compositions that bind or block air pollutants that have an aerodynamic diameter of more than 10 μm.

Short and/or long term exposure to air pollutants (including acute (e.g., single, non-repetitive exposure that does not exceed 8 hours), sub-chronic (e.g., repeated or continuous exposure for up to a 3-month period), and chronic (e.g. repeated or continuous exposure over a period of more than 3 months) exposure) has been associated with a variety of adverse health effects, including increased respiratory and cardiovascular morbidity, such as aggravation of asthma, respiratory diseases and an increase in hospital admissions as well as increased mortality from cardiovascular and respiratory diseases and from lung cancer. Especially vulnerable populations include asthmatics, bronchitis patients, cardiac patients, and young children. Moreover, there is evidence that particulate air pollutants adversely affect neurological diseases, human fertility, and birth outcomes. Some of these associations are discussed in greater detail below and in the references cited herein.

Without being bound by theory, it is believed that air pollutants can adversely affect a subject's lungs (e.g., by causing inflammation, causing oxidative stress, exacerbating and accelerating development of chronic obstructive pulmonary disease, increasing respiratory problems/symptoms, and/or decreasing pulmonary function); reproductive and/or developmental health (e.g., by causing infertility, miscarriage, fetal growth retardation, premature birth, and/or low birth weight); blood (e.g., by causing circulation problems, increased coagulation, particle diffusion through capillary walls, blood clots, reduction in oxygen saturation); circulatory system (e.g., by causing development, acceleration, and/or destabilization of atherosclerotic plaques, endothelial degradation, and/or hypertension); heart (e.g., by causing alterations in cardiac function, oxidative stress, increase in arrhythmias, disruption of electrocardiac function, and/or increase in myocardial ischemia); and/or brain (e.g., by causing increase in cerebral ischemia, cognitive problems, and/or neurodegenerative disease). Air pollutants can also cause systemic inflammation and oxidative stress in a subject (e.g., by causing increase in C reactive protein, causing an increase in pro-inflammatory mediators, and/or activating lymphocytes and platelet cells). Compositions as described herein can be used to treat and/or prevent such risks associated with exposure to air pollutants.

In some embodiments, air pollutants are associated with an increased risk of conditions related to the cardiovascular system, such as heart attack, acute coronary syndrome, myocardial infarction, stroke (e.g., ischaemic stroke), thickening of artery walls, atherosclerosis (e.g., carotid atherosclerosis), atrial arrhythmias, hypertension, thrombosis, vasoconstriction, elevated cerebrovascular resistance, and reduced cerebral blood flow.

In some embodiments, air pollutants are associated with an increased risk of conditions related to the respiratory system, such as chronic obstructive pulmonary disease (COPD), acute lower respiratory diseases, asthma, bronchitis (e.g., chronic bronchitis), bacterial infections in lung tissue, and lung cancer (e.g., adenocarcinoma).

In some embodiments, air pollutants are associated with an increased risk of conditions related to the nervous system and/or conditions characterized by impaired cognitive function. For example, the compositions are useful for treating or preventing neurodegenerative diseases (e.g., Alzheimer's disease, Parkinson's disease), learning delays, impaired memory, impaired reaction time, and/or depression.

In some embodiments, air pollutants are associated with an increased risk of conditions related to the developmental conditions, complications related to pregnancy, and/or postnatal conditions. For example, air pollutants are associated with adverse birth outcomes (e.g., reduced fetal growth, pre-term birth, reduced birth weight, spontaneous abortion, stillbirth, and miscarriage). Air pollutants are also associated with the risk that an unborn child will experience reduced lung function, impaired immune system, allergies, asthma, diabetes, and respiratory death after birth (e.g., as a newborn or later in life).

In some embodiments, air pollutants are associated with increased inflammation, such as cellular inflammation, and/or increased chemokine production. For instance, air pollutants can be associated with a type-1 hypersensitivity response with histamine release, e.g., as discussed in Higgins, Curr. Opin. Otolaryngol. & Head & Neck Surg., 20(3): 209-214 (2012). As a result, air pollutants can be associated with various inflammation-related conditions, such as allergic rhinitis, chronic rhinitis, and/or nasal congestion.

Moreover, air pollutants can be associated with DNA damage in nasal cells. See, e.g., Shusterman, Proc. Am. Thorac. Soc., 8(1): 101-105 (2011), discussing DNA damage observed in exfoliated nasal cells. Without being bound by theory, such DNA damage is believed to occur at higher levels in asthmatic subjects, as discussed, e.g., in Fortoul, Arch. Environ. Health., 58(6): 348-52 (2003).

In some embodiments, air pollutants are associated with secretory hypertrophy of nasal epithelium and/or a shift toward acidic mucus secretion and/or ciliary damage. See, e.g., Camargo Pires-Neto, Environ. Res., 101(3): 356-61 (2006). Such effects can lead to intra- and inter-cellular oedema and increased mucus viscosity, which can adversely impact lung function, such as by causing a decrease in ciliary beat frequency and a decrease in mucuciliary transport and/or impairment of defense mechanisms of the respiratory tract.

In some embodiments, air pollutants exert a pro-inflammatory effect in a subject, such as the generation of oxidative stress. Such an effect can be characterized by increased cytokine and/or chemokine (e.g., macrophage inflammatory proteins, such as MIP-2) production, and/or increased expression of adhesion molecules. See Li, Free radical Biology & Medicine, 44(9): 1689-1699 (2008). In some embodiments, air pollutants are associated with inflammatory biomarkers, such as one or more of tumor necrosis factor alpha (TNF-α) (which, without being bound by theory, is associated with autoimmune disorders such as rheumatoid arthritis, ankylosing spondylitis, inflammatory bowel disease, psoriasis, hidradenitis suppurativa, and refractory asthma), interleukin (IL)-6, and IL-8. In some embodiments, air pollutants are associated with increased systemic or cerebral levels of antibodies associated with inflammation, such as IgE and/or IgG.

In accordance with some embodiments, the compositions described herein are used to treat and/or reduce the risk associated with exposure to air pollutants, e.g., to reduce inflammation and/or an inflammatory response in a subject. For example, some embodiments comprise administering a composition as described herein to decrease serum levels and/or bronchoalveolar lavage fluid levels of IgE in a subject administered the composition. In some embodiments, the composition reduces the risk of an increase of serum levels and/or bronchoalveolar lavage fluid levels of IgE in a subject administered the composition. Some embodiments comprise administering a composition as described herein to decrease serum levels and/or bronchoalveolar lavage fluid levels of TNF-α in a subject administered the composition. In some embodiments, the composition reduces the risk of an increase of serum levels and/or bronchoalveolar lavage fluid levels of TNF-α in a subject administered the composition. Some embodiments comprise administering a composition as described herein to decrease serum levels and/or bronchoalveolar lavage fluid levels of MIP-2 in a subject administered the composition. In some embodiments, the composition reduces the risk of an increase of serum levels and/or bronchoalveolar lavage fluid levels of MIP-2 in a subject administered the composition.

In accordance with some embodiments, the compositions described herein are used to reduce inflammation in a subject in need thereof, e.g., reducing the risk of inflammation in a subject in need thereof by administering a composition as described herein to the subject. In some embodiments, the inflammation is associated with exposure to air pollutants.

In accordance with some embodiments, a compositions as described herein is used to reduce serum and/or bronchoalveolar lavage fluid levels of IgE in a subject in need thereof. In accordance with some embodiments, a compositions as described herein is used to reduce the risk of an increase of serum levels and/or bronchoalveolar lavage fluid levels of IgE in a subject in need thereof. In accordance with some embodiments, a compositions as described herein is used to decrease serum levels and/or bronchoalveolar lavage fluid levels of TNF-α in a subject in need thereof. In accordance with some embodiments, a compositions as described herein is used to reduce the risk of an increase of serum levels and/or bronchoalveolar lavage fluid levels of TNF-α in a subject in need thereof. In accordance with some embodiments, a compositions as described herein is used to decrease serum levels and/or bronchoalveolar lavage fluid levels of MIP-2 in a subject in need thereof. In accordance with some embodiments, a compositions as described herein is used to reduce the risk of an increase of serum levels and/or bronchoalveolar lavage fluid levels of MIP-2 in a subject in need thereof. In any of embodiments, the serum levels and/or bronchoalveolar lavage fluid levels of IgE, TNF-α, and/or MIP-2 may be associated with exposure to air pollutants.

In accordance with some embodiments, a composition as described herein is effective to reduce inflammation and/or reduce the risk of inflammation. Without being bound by theory, the composition may inhibit production of IgE, TNF-α, and/or MIP-2 (e.g., inhibit production of IgE by plasma cells, such as white blood cells). Additionally or alternatively, the composition may bind to IgE, TNF-α, and/or MIP-2. Thus, some embodiments comprise methods of reducing inflammation and/or reducing the risk of inflammation by administering a composition that inhibits production of IgE, TNF-α, and/or MIP-2 (e.g., inhibit production of IgE by plasma cells, such as white blood cells) to a subject in need thereof. Additionally or alternatively, some embodiments comprise methods of reducing inflammation and/or reducing the risk of inflammation by administering a composition that binds to IgE, TNF-α, and/or MIP-2 to a subject in need thereof.

Some embodiments comprise co-administering a composition as described herein with an anti-inflammatory treatment. In some embodiments, the composition is administering before, simultaneous with, or after administration of the anti-inflammatory treatment. In some embodiments, the anti-inflammatory treatment comprises one or more of an antihistamine and/or an anti-leukotriene, a corticosteroid, a bronchodilator, a mast cell stabilizer, and an anti-IgE therapeutic (e.g., omalizumab).

Some embodiments comprise co-administering a composition as described herein with an immunnosuppressive treatment, such as a treatment comprising administration of one or more of the immunnosuppressant agents disclosed above. In some embodiments, the composition is administering before, simultaneous with, or after administration of the immunnosuppressive treatment.

Some embodiments comprise treating and/or reducing the risk of exposure to one or more air pollutants by administering a composition as described herein comprising an agent that binds to one or more air pollutants. Some embodiments comprise treating and/or reducing the risk of exposure to one or more air pollutants by administering a composition as described herein that blocks one or more air pollutants. In some embodiments, the composition neutralizes the effects of one or more air pollutants. In some embodiments, the composition acts as antagonist against the effects of one or more air pollutants. In some embodiments, the composition protects against adverse effects of one or more air pollutants. In some embodiments, the composition desensitizes a subject to adverse effects associated with one or more air pollutants. In some embodiments, the composition is beneficial to a subject exposed to one or more air pollutants.

Also provided are compositions as described herein for use in treating and/or reducing risks of exposure to air pollutants. Also provided are uses of the compositions as described herein in the preparation of medicaments for treating and/or reducing risks of exposure to air pollutants.

The following examples are included as illustrative of the compositions described herein. These examples are in no way intended to limit the scope of the invention. Other aspects of the invention will be apparent to those skilled in the art to which the invention pertains.

EXAMPLES

Example 1—Formulation of Nasal Compositions

Nasal compositions in the form of gels comprising castor oil, oleoyl polyoxylglycerides (LABRAFIL® apricot kernel oil PEG-6-esters from Gattefosse), and silicon dioxide were prepared having the formulations set forth in Table 2. Specifically, the LABRAFIL® was added to the castor oil, and then mixed for 2 minutes at 13,000 rpm using an ULTRATURRAX® disperser. The silicon dioxide component was then added, homogenized slightly by hand, and mixed for 10 minutes at 13,000 rpm using an ULTRATURRAX® disperser.

TABLE 2

Formulations For Compositions 1-3

|  | Composition 1 | Composition 2 | Composition 3 |
|---|---|---|---|
| Castor Oil | 92% | 91% | 91% |
| Labrafil ® | 4% | 4% | 4% |
| Silicon Dioxide Component | 4% (AEROSIL ® 200) | 5% (SYLOID ® AL-1FP) | 5% (SYLOID ® 244 FP) |

The viscosity of the compositions was tested using a spreading test. Specifically, a portion of each composition (about 50 mg) was applied to a slide, and then a second slide was placed on top of the first slide to apply pressure to the composition. The extent of spreading of each composition was assessed by measuring the diameter of the composition 2 minutes and 10 minutes after the second slide was applied. The measured diameters are set forth in Table 3.

TABLE 3

Results of Spreading Test on Compositions 1-3

|  | Composition 1 | Composition 2 | Composition 3 |
|---|---|---|---|
| Diameter after 2 minutes | 1.2 cm | 4.5 cm | 2.1 cm |
| Diameter after 10 minutes | 1.2 cm | Composition flowed off of slide | 2.3 cm |

SYLOID® AL-IFP Compositions

Compositions similar to Composition 2, but with varying amounts of SYLOID® AL-1FP, were prepared and the viscosity of the compositions was evaluated using the spreading test. Results of the spreading test are set forth in Table 4.

TABLE 4

Results of Spreading Test on Compositions with SYLOID ® AL-1FP

| Composition | Amount of SYLOID ® AL-1FP | Diameter after 2 minutes | Diameter after 10 minutes |
|---|---|---|---|
| Composition 4 | 15% (Composition 2 + 117 mg SYLOID ® AL-1FP) | 4.0 cm | 5.6 cm |
| Composition 5 | 30% (Composition 2 + 357 mg SYLOID ® AL-1FP) | 3.1 cm | 4.5 cm |
| Composition 6 | 40% (Composition 2 ± 583 mg SYLOID ® AL-1FP) | 2.5 cm | 3.1 cm |
| Composition 7 | 50% (Composition 2 + 900 mg SYLOID ® AL-1FP) | 1.7 cm | 1.8 cm |

The results showed that the viscosity of the composition could be adjusted by varying the amount of SYLOID® AL-1FP. However, the composition with 50% SYLOID® AL-1FP was not as supple as the reference composition (Composition 1) and had a grayish color.

SYLOID® AL-IFP/AEROSIL® Combination Compositions

Compositions with both SYLOID® AL-1FP and AEROSIL® 200 were prepared, and the viscosity of the compositions was measured using the spreading test. These results are set forth in Table 5.

TABLE 5

Formulas and Spreading Test Results for SYLOID® AL-1FP Compositions

|  | Castor Oil | LABRAFIL® | SYLOID® AL-1FP | AEROSIL® | Diameter after 2 minutes |
|---|---|---|---|---|---|
| Composition 8 | 6.4 g | 0.4 g | 3.0 g (30%) | 0.2 g (2%) | 2.8 cm |
| Composition 9 | 6.4 g | 0.4 g | 3.0 g (20%) | 0.3 g (3%) | 2.5 cm |
| Composition 10[a] | 7.2 g | 0.4 g | 2.0 g (20%) | 0.4 g (4%) | 3.0 cm |
| Composition 11[a] | 7.2 g | 0.4 g | 2.0 g (20%) | 0.4 g (4%) | 2.7 cm |
| Composition 12 | 6.8 g | 0.4 g | 2.0 g (20%) | 0.8 g (8%) | 2.3 cm |
| Composition 13 | 6.1 g | 0.4 g | 2.0 g (20%) | 1.5 g (15%) | 1.7 cm |
| Composition 14 | 7.8 g | 0.4 g | 1.0 g (10%) | 0.8 g (8%) | 2.7 cm |
| Composition 15 | 7.1 g | 0.4 g | 1.0 g (10%) | 1.5 g (15%) | [b]1.6 cm |
| Composition 16 | 7.6 g | 0.4 g | 0.5 g (5%) | 1.5 g (15%) | 1.3 cm |
| Composition 17 | 6.6 g | 0.4 g | 1.5 g (15%) | 1.5 g (15%) | 1.7 cm |
| Composition 18 | 6.9 g | 0.4 g | 1.5 g (15%) | 1.2 g (12%) | 2.0 cm |
| Composition 19 | 7.9 g | 0.4 g | 0.5 g (5%) | 1.2 g (12%) | 1.8 cm |

[a]In Composition 10, the SYLOID® AL-1FP was added to the composition before the AEROSIL®. In Composition 11, the AEROSIL® was added to the composition before the SYLOID® AL-1FP. Compositions 12-19 were prepared by adding the AEROSIL® before the SYLOID® AL-1FP.
[b]A spread test conducted after storing the composition at room temperature for 2.5 days showed a 1.3 cm diameter. Experiments that included stirring the stored composition before conducting the spread test showed a diameter of 1.1 cm.

The results show that the viscosity of a composition increases with increased amounts of SYLOID® AL-1FP. The results also show that higher amounts of SYLOID® AL-1FP can be incorporated into the composition if AEROSIL® is added before adding the SYLOID® AL-1FP.

A rod test was conducted to assess flowability of Compositions 13-19, wherein Composition 14 showed the most flowability, Compositions 13 showed substantially no flowability, and Compositions 15-18 showed little flowability.

All gels prepared with SYLOID® AL-1FP and AEROSIL® produced threads when stretched, whereas compositions prepared with AEROSIL® (but not SYLOID® AL-1FP) tore when stretched.

SYLOID® 244 FP Compositions

Compositions similar to Composition 3, but with varying amounts of SYLOID® 244 FP, were prepared. The viscosity of the compositions was evaluated using the spreading test, and the flowability was measured using the rod test. Results of the spreading test are set forth in Table 6.

TABLE 6

Formulas and Spreading Test Results for SYLOID® 244 FP Compositions

| Composition | Amount of SYLOID® 244 FP | Diameter after 2 minutes | Diameter after 10 minutes |
|---|---|---|---|
| Composition 20 | 6.9% (Composition 3 + 20 mg SYLOID® 244 FP) | 1.6 cm | 1.6 cm |
| Composition 21 | 7.8% (Composition 3 + 30 mg SYLOID® 244 FP) | 1.4 cm | 1.4 cm |
| Composition 22 | 8.7% (Composition 3 + 40 mg SYLOID® 244 FP) | 1.2 cm | 1.2 cm |

The 8.7% SYLOID® 244 FP composition had a similar viscosity, feel, and adhesion characteristics as the reference composition.

Compositions with Added Silicon Dioxide Gelling Agents

Compositions similar to Composition 1, but with added silicon dioxide gelling agents, were prepared. Viscosity (via the spreading test) and flowability of the compositions were measured. In the rod test, all compositions showed little to substantially no flowability. The formulations for these compositions are set forth in Table 7.

TABLE 7

Formulations and Spreading Test Results for Compositions with Added Gelling Agent

| Composition | Castor Oil | LABRAFIL® | AEROSIL® | Added Gelling Agent | Diameter after 2 min |
|---|---|---|---|---|---|
| Composition 1a | 16.4 g | 0.8 g | 0.8 g | — | 1.2 cm |
| Composition 23 | 46.5 g | 2.0 g | 1.5 g | — | 1.5 cm |
| Composition 24 | 46.5 g | 2.0 g | 1.5 g | 10 mg SYLODENT® SM 880 T (1%) | 1.2 cm |
|  | 46.5 g | 2.0 g | 1.5 g | 20 mg | 1.2 cm |

TABLE 7-continued

Formulations and Spreading Test Results for Compositions with Added Gelling Agent

| Composition | Castor Oil | LABRAFIL ® | AEROSIL ® | Added Gelling Agent | Diameter after 2 min |
|---|---|---|---|---|---|
| Composition 25 | | | | SYLODENT ® SM 880 T (2%) | |
| Composition 26 | 46.5 g | 2.0 g | 1.5 g | 31 mg SYLODENT ® SM 880 T (3%) | 1.1 cm |
| Composition 27 | 46.5 g | 2.0 g | 1.5 g | 42 mg SYLODENT ® SM 880 T (4%) | 1.0 cm |
| Composition 28 | 46.5 g | 2.0 g | 1.5 g | 5 mg SYLOBLANC ® 34 (0.5%) | 1.2 cm |
| Composition 29 | 46.5 g | 2.0 g | 1.5 g | 10 mg SYLOBLANC ® 34 (1%) | 1.2 cm |
| Composition 30 | 46.5 g | 2.0 g | 1.5 g | 15 mg SYLOBLANC ® 34 (1.5%) | 1.2 cm |
| Composition 31 | 46.5 g | 2.0 g | 1.5 g | 20 mg SYLOBLANC ® 34 (2%) | 1.1 cm |
| Composition 32 | 46.5 g | 2.0 g | 1.5 g | 30 mg SYLOBLANC ® 34 (3%) | 1.2 cm |
| Composition 33 | 46.5 g | 2.0 g | 1.5 g | 50 mg SYLOBLANC ® 34 (4.8%) | 0.9 cm |

In the rod test for Compositions 1a and 23-27, all compositions showed substantially no flowability. The compositions had comparable viscosity and adhesion. Moreover, the compositions were supple, could be easily stirred, and were visually similar.

In the rod test for Compositions 1a, 23, and 28-33, all compositions showed substantially no flowability. The gels had comparable viscosity and adhesion. Moreover, the compositions were supple, could be easily stirred, and were visually similar.

A moist slide test was conducted with all gels in Table 7. In particular, water was applied to a slide, and then the gel was applied to the water surface, and the slide was titled. All tested gels remained positioned on the slide, even though the tilting displaced the water from the slide.

Example 2—Evaluation of Protection Against Air Pollutants

A 10-day study is conducted to test efficacy of nasal compositions in reducing risks of exposure of rats to airborne dust particles. A composition as described herein is administered intranasally to rats, and then the rats are exposed to a Standard Reference Material (SRM) dust by inhalation. Specifically, the composition is administered to a first group of rats. A second group of rats is not administered the composition. Both the first and second groups are exposed to SRM dust using a TSE inhalation system at 10 mg/m3. A third group of rats is untreated but exposed to filtered air using the TSE inhalation system.

All tested animals are observed daily throughout the study, and body weight, water consumption, and food consumption are recorded. Urine samples are collected daily for measurement of (a) concentration of metals (e.g., Pb and Cd) using ICP-MS and (b) metabolites of polycyclic aromatic hydrocarbons (e.g., 1-hydroxypyrene, 3-hydroxyphenanthrene, and 1-aminopyrene) by HPLC/FLD. Blood samples are collected from the tail vein every two days for measurement of metals Pb and Cd using ICP-MS. A full hematological examination on the blood samples is also conducted, which includes measurement of hemoglobin concentration, hematocrit, red blood cells, white blood cells, platelet count, white blood cell differential, clotting potential (prothrombin time and fibrinogen concentration), total protein concentration, albumin concentration, total cholesterol, HDL and LDL fraction concentration, glucose concentration, creatinine concentration, uric acid concentration, triglycerides concentration, urea nitrogen concentration, and ALT and AST activity. Genotoxicity testing is conducted using a comet assay in peripheral blood leukocytes isolated at sacrifice from all rats.

At day 11, the rats are sacrificed for cytological and histopathological analysis. Cytological analysis is performed after washing of the nasal cavity, paranasal sinuses and lungs (bronchioalveolar lavage (BAL) fluid) with PBS. The following determinations are performed from the BAL fluid: WBC differential, total protein concentration, LDH activity, markers of oxidative/antioxidative processes, e.g. MDA, TAS, GPx activity, TNF-α and macrophage inflammatory protein-2 (MIP-2) by ELISA. Samples of nasal mucosa are then collected, and the lungs, liver, kidney and brain are harvested for histopathological examination.

Toxicokinetic and toxicological endpoints known to be linked with exposure to air pollutants are evaluated. Primary endpoints include (i) the level of metabolites of polycyclic aromatic hydrocarbons in urine, (ii) the level of heavy metals in blood and urine, and (iii) histopathological analysis. Diminished toxic effects in rats administered the nasal gel will show a protective effect of the gel against toxicity of environmental and/or occupational particulate matter. A schematic of the study is set forth in Table 8.

TABLE 8

Evaulation of protection of mucosa against airborne dust particles

| Group No. | Treatment/exposure continuously for 10 days | Determinations |
|---|---|---|
| 1 | Composition (intranasal)/ SRM dust (inhalation) | Blood: Heavy metals every 2 days, hematology and biochemistry every 2 days<br>Urine: Heavy metals, PAH metabolites every 2 days<br>Cytology, BAL and histopathology at necropsy |
| 2 | SRM dust (inhalation) | Blood: Heavy metals every 2 days, hematology and biochemistry every 2 days<br>Urine: Heavy metals, PAH metabolites every 2 days<br>Cytology, BAL and histopathology at necropsy |
| 3 | Filtered Air | Blood: Heavy metals every 2 days, hematology and biochemistry every 2 days<br>Urine: Heavy metals, PAH metabolites every 2 days<br>Cytology, BAL and histopathology at necropsy |

Example 3—Evaluation of Inflammation Markers

A 10-day study was conducted to test efficacy of nasal compositions in reducing inflammatory markers. A composition as described herein comprising 8.7% w/w colloidal hydrated silica (e.g., Syloid® 244 FP), 4.0% w/w oleoyl polyoxyl-6 glycerides (e.g., Labrafil®), and 87.3% w/w castor oil was administered intranasally to rats, and then the rats were exposed to Standard Reference Material (SRM), a representative dust, by inhalation. Specifically, the composition was administered to a first group of rats, and a second group of rats was not administered the composition. Both the first and second groups were exposed to SRM dust using a TSE inhalation system at 10 mg/m3. A third group of rats was untreated but exposed to filtered air using the TSE inhalation system. A fourth group of rats was treated with the composition, but was not exposed to SRM dust. A schematic of the study is set forth in Table 9.

TABLE 9

Evaulation of protection by the composition against inflammation

| Group No. | Treatment/exposure continuously for 10 days | Determinations |
|---|---|---|
| 1 | Composition (intranasal)/SRM dust (inhalation) | Blood: TNFα, IgE<br>BAL: TNFα, MIP2 |
| 2 | SRM dust (inhalation) | Blood: TNFα, IgE<br>BAL: TNFα, MIP2 |
| 3 | Filtered Air (control) | Blood: TNFα, IgE<br>BAL: TNFα, MIP2 |
| 4 | Composition (intranasal) | Blood: TNFα, IgE<br>BAL: TNFα, MIP2 |

All tested animals were observed daily throughout the study, and body weight, water consumption, and food consumption were recorded. At day 11, the rats were sacrificed. At both the beginning of the study (pre-exposure; i.e., before exposure to gel/dust/air) and/or after sacrifice of the rats, the presence of the following inflammatory markers was determined from either serum or bronchoalveolar lavage (BAL) fluid by ELISA: IgE (determined pre-exposure and after sacrifice), TNF-α (determined after sacrifice), and MIP2 (determined after sacrifice). Serum levels of TNF-α and IgE are set forth in Table 10. BAL fluid levels of TNF-α and MIP-2 are set forth in Table 11. Additional results are reported in FIGS. 2A-E, which report results as mean±standard deviation.

TABLE 10

Serum Levels of TNFα and IgE

| | | IgE, ng/ml | |
|---|---|---|---|
| | TNF-α, ng/l | Before exp. | After exp. |
| Group 1 (Gel + dust) | 40.10 ± 1.23 | 2.73 ± 0.69 | 3.64 ± 0.95 |
| Group 2 (Dust) | 40.85 ± 0.72 | 3.11 ± 0.92 | 10.28 ± 3.27 |
| Group 3 (Control) | 39.17 ± 0.93 | 2.71 ± 0.82 | 2.96 ± 0.58 |
| Group 4 (Gel) | 39.88 ± 1.22 | 2.74 ± 0.82 | 4.09 ± 3.06 |

TABLE 11

BAL Levels of TNF-α and MIP-2

| | TNF-α, ng/l | MIP2, pg/ml |
|---|---|---|
| Group 1 (Gel + dust) | 13.2 ± 0.9 | 53.0 ± 14.1 |
| Group 2 (Dust) | 14.6 ± 1.5 | 58.7 ± 37.7 |
| Group 3 (Control) | 12.9 ± 0.5 | 49.3 ± 16.4 |
| Group 4 (Gel) | 12.5 ± 0.4 | 46.2 ± 8.2 |

Figure 2A:
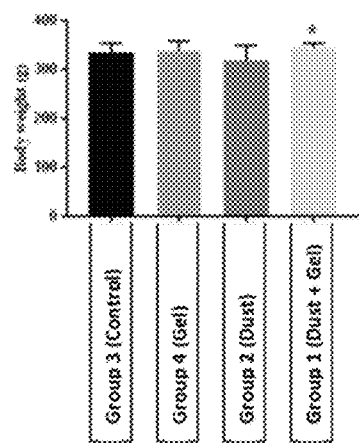
FIGS. 2A-E show results of an in vivo study of the efficacy of a nasal composition as described herein.
Figure 2B:
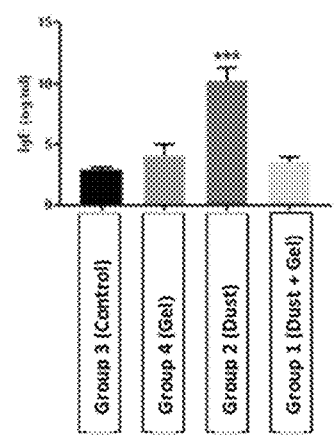
Figure 2C:
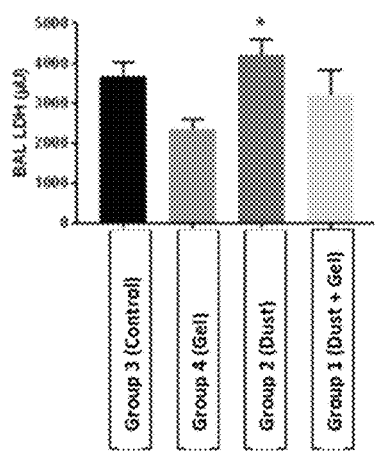
Figure 2D:
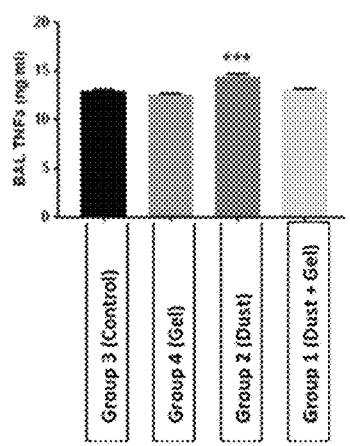
Figure 2E:
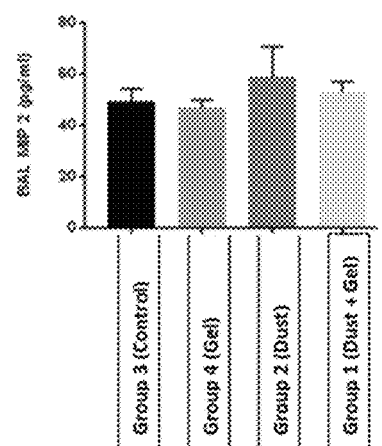

FIG. 2A shows a shows a positive impact on body weight (g) (ANOVA $F(3,36)=2.41$; $P=0.08$; *$p \leq 0.05$ by t-test as compared to Group 1). FIG. 2B shows protection against an increase in serum IgE levels (ng/ml) induced by exposure to dust (ANOVA $F(3,36)=21.6$; $P=\leq 0.001$; ***$p \leq 0.001$ as compared to Groups 1, 3, and 4). FIG. 2C shows protection against an increase in BAL LDH levels induced by exposure to dust (μU) (ANOVA $F(3,3-)=3.456$; $P=\leq 0.05$; *$p \leq 0.05$ as compared to Group 4). FIG. 2D shows protection against an increase in BAL TNF-α levels induced by exposure to dust (ng/ml) (ANOVA $F(3,36)=28.72$; $P=\leq 0.001$; ***$p \leq 0.001$ as compared to Groups 1, 3, and 4). FIG. 2E shows a trend towards protection against an increase in BAL MIP2 levels induced by exposure to dust (pg/ml) (ANOVA $F(3,36)=0.6$; $P=0.61$).

The data show that IgE serum levels were significantly decreased in rats administered the composition prior to exposure to dust, as compared to rats exposed to dust that were not treated with the composition. The data also show that TNF-α and MIP-2 levels were lower in in rats administered the composition prior to exposure to dust, as compared to rats exposed to dust that were not treated with the composition.

Example 4—Study to Assess Anti-Inflammatory and Anti-Allergy Efficacy

This study will assess the efficacy of a composition as described herein against environmental risks caused by solid and liquid particles suspended in the air. Effects of high air particulate matter levels include increased IgE serum levels, increased eosinophils numbers, induction of the proinflammatory cytokine TNFα, and asthma and wheezing episodes. These air pollution-induced responses are measurable and can be used as indicators to evaluate the protective effects of compositions as described herein. Patients suffering from allergic rhinitis and/or asthma are particularly sensitive to increased air particulate matter. The study will be conducted by exposing subjects with allergic rhinitis and healthy subjects to air pollution in an allergen challenge chamber.

The rhinitis subjects may be selected based on, for example, having positive skin prick test results, a total nasal symptom score (TNSS) of at least 6 during a 4-hour screening exposure in the allergen exposure chamber (AEC), and/or symptomatic or with mild symptoms (TNSS<3 and a score<2 for each individual symptom) at the time of inclusion and before each allergen challenge. Rhinitis patients may be excluded based on, for example, structural nasal defect, nasal polyps, infection of the upper air-ways within 4 weeks of study entry, sinusitis, asthma (except mild intermittent asthma using b2-agonists only), pregnancy/breastfeeding, current immunotherapy, known hypersensitivity, and participation in another clinical trial within 30 days of study enrollment.

The healthy subjects may be selected based on, for example, having no history of allergic rhinitis, and negative skin prick test result to 15 major aerochallenges.

Subjects will be exposed to allergens for 4 hours on two occasions in an allergen exposure chamber. The two exposures to allergens will be separated by 21 days. Immediately before the allergen challenge, the subjects will be administered a composition as described herein (e.g., comprising 8.7% w/w colloidal hydrated silica (e.g., Syloid® 244 FP), 4.0% w/w oleoyl polyoxyl-6 glycerides (e.g., Labrafil®), and 87.3% w/w castor oil) into both nostrils. After each challenge, changes compared to baseline levels of the following allergen response factors may be measured: β-tryptase, Prostaglandin D2 (PGD2), total and allergen specific Immunoglobulin E (IgE) and IgG antibodies, eosinophil, interleukin (IL) 5, IL-6, IL-13, Chemokine ligand 3 and 4 (CCL3 and CCL4), Tumor Necrosis Factor (TNF-α), Lactate Dehydrogenase (LDH), nitric oxide. In addition, the subject's nasal flow rate, and nasal symptoms like obstruction, rhinorrhea, sneezing, and itching, may be measured.

Statistical analysis of the results may be performed by comparing variables before and after the challenges separately for each group and challenge day by using a paired t test. An unpaired t test may be used to compare groups with respect to the mean changes from before to after challenge time points. In a secondary analysis, the correlation between TNSS and a subset of cells and cytokines found to be specific for patients with allergic rhinitis in the primary analysis may be calculated using the Spearman correlation coefficient.

REFERENCES

The following references are incorporated herein by reference to the extent that they discuss an association between air pollutants and health risks:

Camargo Pires-Neto R et al, "Effects of Sao Paulo air pollution on the upper airways of mice," Environ Res., 101(3): 356-61 (2006).

Fortoul T I et al., "Single-cell gel electrophoresis assay of nasal epithelium and leukocytes from asthmatic and non-asthmatic subjects in Mexico City," Arch Environ Health, 58(6): 348-52 (2003).

Higgins T S et al., "Environmental pollutants and allergic rhinitis," Curr Opin Otolaryngol Head Neck Surg., 20(3): 209-14 (2012).

Phalen R F, "The particulate air pollution controversy," Nonlinearity Biol Toxicol Med, 2(4): 259-92 (2004).

Shusterman D, "The effects of air pollutants and irritants on the upper airway," Proc Am Thorac Soc., 8(1): 101-5 (2011) (doi: 10.1513/pats.201003-027RN)

Tunaru S et al., "Castor oil induces laxation and uterus contraction via ricinoleic acid activating

What is claimed is:

1. A method for reducing the risks of exposure to air pollutants in a subject in need thereof, comprising nasally administering to the subject an effective amount of a composition comprising an agent that binds to one or more air pollutants, wherein the agent comprises one or more of nonporous silicon dioxide and porous silicon dioxide, wherein the composition is effective to block the one or more air pollutants from entering the body of the subject via the nasal cavity, thereby reducing the risk of exposure to air pollutants.

2. The method of claim 1, wherein the risks of exposure to air pollutants comprise health problems associated with one or more of the cardiovascular system, the respiratory system, the nervous system, and the reproductive system.

3. The method of claim 1, wherein the agent comprises a colloidal silicon dioxide.

4. The method of claim 1, wherein the agent comprises an inorganic porous material selected from microporous silicon dioxide, mesoporous silicon dioxide, macroporous silicon dioxide, polyorganosiloxanes, pharmaceutical clays, silicon dioxide nanotubes, silicon dioxide gel, magnesium alumosilicate, anhydrous calcium phosphate, and calcium carbonate.

5. The method of claim 1, wherein the agent is functionalized with one or more of thiol groups, amine groups, crown ethers, quaternary alkyl amines, alkyl chains, alkoxysilanes, fluorenylmethoxycarbonyl-modified organosilanes, hydrophobic groups, mercaptopropyl groups, aminopropyl groups, hydroxypropyl groups, and phenyl groups.

6. The method of claim 1, wherein the composition further comprises one or more of (i) a lipophilic or partly lipophilic vehicle and (ii) a surfactant.

7. The method of claim 6, wherein the lipophilic or partly lipophilic vehicle comprises an oil or a mixture of oils, fatty acid esters, medium chain triglycerides, glycerol esters of fatty acids, polyethylene glycol, phospholipids, white soft paraffin, or combinations of two or more thereof.

8. The method of claim 6, wherein the surfactant comprises apricot kernel oil PEG 6 esters, lecithin, fatty acid esters of polyvalent alcohols, fatty acid esters of sorbitanes, fatty acid esters of polyoxyethylenesorbitans, fatty acid esters of polyoxyethylene, fatty acid esters of sucrose, fatty acid esters of polyglycerol, oleoyl polyoxylglycerides, oleoyl macrogolglycerides, sorbitol, glycerine, polyethylene glycol, macrogol glycerol fatty acid ester, or combinations of any two or more thereof.

9. The method of claim 1, wherein the composition comprises
   (a) from about 0.5% to about 50% w/w of a colloidal silicon dioxide agent, based on the weight of the composition, (b) from about 50% to about 98% w/w of castor oil, based on the weight of the composition, and (c) from about 0.5% to about 20% w/w a oleoyl polyoxyl-6 glycerides, based on the weight of the composition.

10. The method of claim 1, wherein the composition further comprises an immunosuppressive agent.

11. The method of claim 10, wherein the immunosuppressive agent comprises one or more selected from antibodies against a cytokine selected from IL-2, IL-4, IL-5, IL-13, and TNF-α, anti-IgE antibodies, glucocorticoids, antibiotics, polysaccharides, and antihistamines.

12. The method of claim 1, wherein the method reduces the risk of inflammation in the subject.

13. The method of claim 1, wherein the method reduces the serum IgE levels in the subject.

14. The method of claim 1, wherein the method reduces serum TNF-α levels in the subject.

15. The method of claim 1, wherein the method reduces MIP-2 levels in the subject.

16. A nasal composition for reducing the risks of exposure to air pollutants in a subject in need thereof, comprising (i) an effective amount of an agent that binds to one or more air pollutants and is selected from one or more of nonporous silicon dioxide and porous silicon dioxide, (ii) a lipophilic or partly lipophilic vehicle, and (iii) a surfactant, wherein the composition is adapted for nasal administration and does not include a pharmaceutically active agent.

17. The composition of claim 16, wherein the agent is a colloidal silicon dioxide.

18. The composition of claim 16, wherein the agent comprises an inorganic porous material selected from microporous silicon dioxide, mesoporous silicon dioxide, macroporous silicon dioxide, polyorganosiloxanes, pharmaceutical clays, silicon dioxide nanotubes, silicon dioxide gel, magnesium alumosilicate, anhydrous calcium phosphate, and calcium carbonate.

19. The composition of claim 16, wherein the agent is functionalized with one or more selected from thiol groups, amine groups, crown ethers, quaternary alkyl amines, alkyl chains, alkoxysilanes, fluorenylmethoxycarbonyl-modified organosilanes, hydrophobic groups, mercaptopropyl groups, aminopropyl groups, hydroxypropyl groups, and phenyl groups.

20. A nasal composition for reducing the risks of exposure to air pollutants in a subject in need thereof, comprising (i) an agent that binds to one or more air pollutants and is selected from one or more of nonporous silicon dioxide and porous silicon dioxide, (ii) a lipophilic or partly lipophilic vehicle, (iii) a surfactant, and (iv) an immunosuppressive agent, wherein the composition is adapted for nasal administration.

21. The composition of claim 20, wherein the immunosuppressive agent comprises one or more selected from antibodies against a cytokine selected from IL-2, IL-4, IL-5, IL-13, and TNF-α, anti-IgE antibodies, glucocorticoids, antibiotics, polysaccharides, and antihistamines.

* * * * *